US006843987B2

(12) United States Patent
Debets et al.

(10) Patent No.: US 6,843,987 B2
(45) Date of Patent: Jan. 18, 2005

(54) MAMMALIAN CYTOKINES; RECEPTORS; RELATED REAGENTS AND METHODS

(75) Inventors: Johannes Eduard Maria Antonius Debets, Rhoon (NL); Jacqueline C. Timans, Mountain View, CA (US); J. Fernando Bazan, Palo Alto, CA (US); Robert A. Kastelein, Redwood City, CA (US)

(73) Assignee: Schering Corporation, Kenilworth, NJ (US)

( * ) Notice: Subject to any disclaimer, the term of this patent is extended or adjusted under 35 U.S.C. 154(b) by 168 days.

(21) Appl. No.: 09/775,046

(22) Filed: Feb. 1, 2001

(65) Prior Publication Data

US 2002/0102234 A1 Aug. 1, 2002

Related U.S. Application Data

(60) Provisional application No. 60/179,638, filed on Feb. 2, 2000.

(51) Int. Cl.[7] .................... A61K 45/00; A61K 38/00; C07K 17/00; C07K 16/00; C12P 21/04

(52) U.S. Cl. .................. 424/85.2; 424/85.1; 424/158.1; 514/2; 530/351; 530/388.1; 530/389.1; 435/69.52

(58) Field of Search ............................... 424/85.2, 85.1, 424/158.1; 530/351, 388.1, 389.1; 514/2; 435/69.52

(56) References Cited

U.S. PATENT DOCUMENTS 5,863,769 A * 1/1999 Young ..................... 435/69.52
6,054,559 A * 4/2000 Young ....................... 530/351

FOREIGN PATENT DOCUMENTS

| EP | 0 855 404 A1 | 7/1998 |
|---|---|---|
| WO | WO 99/35268 | 7/1999 |
| WO | WO 99/36541 | 7/1999 |
| WO | WO 99/37662 | 7/1999 |
| WO | WO 96/07739 | 3/2002 |

OTHER PUBLICATIONS

McColl and Lewis, J. Immunol. 1999, vol. 163(5), pp. 2829–2835.*
Jenny L. Barton, et al., Eur. J. Immunol., 30:3299–3308, 2000. "A tissue specific IL–1 receptor antagonist homolog from the IL–1 cluster lacks IL–1 cluster lacks IL–1, IL–1ra, IL–18 and IL–18 antagonist activities".
J. Fernando Bazan, et al., Nature, 379:591, February 15, 1996. "A newly defined interleukin–1?".
Teresa L. Born, et al., J. Biological Chemistry, 273(45):29445–29450, Nov. 6, 1998. "Cloning of a Novel Receptor Subunit, AcPL, Required for Interleukin–18 Signaling".

Alain Carrie, et al., Nature Genet., 23:25–31, Sep. 1999. "A new member of the IL–1 receptor family highly expressed in hippocampus and involved in X–linked mental retardation".
M. Dale and MJ Nicklen, Genomics, 57:177–179, 1999. "Interleukin–1 receptor cluster: gene organization of IL1R2, IL1R1, IL1RL2 (IL–1Rrp2), IL1RL1 (T1/ST2), and IL18R1 (IL–1Rrp) on human chromosome 2q".
R. Debets, et al., EMBL Database, Accession No. AF206696, Dec. 1, 2000. "Novel IL–1 family member IL–1e respondes through the orphan IL–1R related protein 2; response is antagonized by IL–1d".
Charles A. Dinarello, Blood, 87(6):2095–2147, Mar. 15, 1996. "Biologic basis for interleukin–1 in disease".
Tariq Ghayur, et al., Nature, 386(6625):619–623, Apr. 10, 1997. "Caspase–1 processes IFN–gamma–inducing factor and regulates LPS–induced IFN–gamma production".
Yong Gu, et al,. Science, 275(5297):206–209, Jan. 10, 1997. Activation of interferon–gamma inducing factor mediated by interleukin–1beta converting enzyme.
Hirotada Kojima, et al., Biochem, Biophys, Res. Commun., 244(1):183–186, Mar. 6, 1998. "Interleukin–18 activates the IRAK–TRAF6 pathway in mouse EL–4 cells".
Sanjay Kumar, et al., J. Biol. Chem., 275(14):10308–10314, Apr. 7, 2000. "Identification and Initial Characterization of Four Novel Members of the Interleukin–1 Family".
Timothy W. Lovenberg, et al., J. Neuroimmunol., 70:113–122, 1996. "Cloning of a cDNA encoding a novel interleukin–1 receptor related protein (IL1R–rp2)".
M. Marra, et al., GenBank, Accession No. AA030324, Aug. 19, 1996. "The WashU–HHMI Mouse EST Project".
M. Marra, et al., GenBank, Accession No. WO8205, Apr. 25, 1996. "The WashU–HHMI Mouse EST Project".
Julio J. Mulero, et al., Biochem, Biophys. Res. Commun., 263(3):702–706, Oct. 1999. "IL1HY1: A Novel Interleukin–1 Receptor Antagonist Gene".
Luke A.J. O'Neill and Catherine Greene, J. Leukoc. Biol., 63(6):650–657, Jun. 1998. "Signal transduction pathways activated by the IL–1 receptor family: ancient signaling machinery in mammals, insects, and plants".
Patricia Parnet, et al., J. Biological Chemistry, 271(8):3967–3970, Feb. 23, 1996. "IL–1Rrp Is a Novel Receptor–like Molecule Similar to the Type I Interleulin–1 Receptor and Its Homologues T1/ST/2 and IL–1R AcP".
Douglas Robinson, et al., Immunity, 7:571–581, Oct. 1997. "IGIF Does Not Drive Th1 development but Synergizes with IL–12 for Interferon–γ Production and Activates IRAK and NFκB".

(List continued on next page.)

Primary Examiner—Janet Andres
(74) Attorney, Agent, or Firm—Edwin P. Ching; Sheela Mohan-Peterson

(57) ABSTRACT

Nucleic acids encoding mammalian, e.g., rodent, IL-1δ, IL-1ε, purified IL-1δ and IL-1ε proteins and fragments thereof. Antibodies, both polyclonal and monoclonal, are also provided. Methods of using the compositions for both diagnostic and therapeutic utilities are provided.

5 Claims, 1 Drawing Sheet

OTHER PUBLICATIONS

Fernando Rock, et al., *P.N.A.S. USA*, 95:588–593, Jan. 1998. "A family of human receptors structurally related to *Drosophilia* Toll".

Dirk E. Smith, et al., *J. Biol. Chem.*, 275(2):1169–1175, Jan. 14, 2000. "Four New Members Expand the Interleukin–1 Superfamily".

Elisabeth Thomasson, et al., *Cytokine* 11(6):389–399, Jun. 1999. "Identification and Characterization of SIGIRR, A Molecule Representing a Novel Subtype of the IL–1r Superfamily".

Kakuji Torigoe, et al., *J. Biol. Chem.*, 272(41): 25737–25742, Oct. 10, 1997. "Purification and Characterization of the Human Interleukin–18 Receptor".

Shimpei Ushio, et al. *J. Immunol.*, 156:4274–4279, 1996. "Cloning of the cDNA for Human IFN–γ–Inducing Factor, Expression in *Escherichia coli*, and Studies on the Bilogical Activities of the Protein".

Lawrence Weissbach, et al., *Biochem Biophys Res Commun*, 244(1):91–95, Mar. 6, 1998. "Detection of an interleukin–1 intracellular receptor antagonist mRNA variant".

\* cited by examiner

```
hIL-1α       ...MRIIKYEFILNDALNQSIIRAND-Q
hIL-1β       ...APVRSLNCTLRDSQQKSLVMSGP-Y
hIL-1RA      ...KSSKMQAFRIWDVNQKTFYLRN--N
mIL-1γ       ...NFGRLHCTTAVIRNIND---QVLFVDKR-Q
hIL-1γ       ...YFGKLESKLSVIRNLND---QVLFIDQGNR
mIL-1ε       ...EKELRAASPSLRHVQDLSSRVWILQN--N
hIL-1ε       ...RAVYQSMCKPITGTINDLNQQVWTLQG--Q    40
mIL-1δ       ...VLSGALCFRMKDSALKVLYLHN--N
hIL-1δ       MVLSGALCFRMKDSALKVLYLHN--N             24 hIL-1α       YLTAAALHNLDEA----VKFDMGAYKSSKDDA--KITVILRIS-KTQLYV
hIL-1β       ELKALHLQGQDMEQQ--VVFSMSFVQ--GEESNDKIPVALGLK-EKNLYL
hIL-1RA      QLVAGYLQGPNVNLE-EKIDVVPIE---------PHALFLGIH-GGKMCL
mIL-1γ       PVFEDMTDIDQSASEPQTRLIIYMYK---DSEVRGLAVTLSVKDSKMSTL
hIL-1γ       PLFEDMTDSDCRDNAPRTIFIISMYK---DSQPRGMAVTISVKCEKISTL
mIL-1ε       ILTAVPRKEQTV---PVTITLLPCQYLDTLETNRGDPTYMGVQ-RPMSCL
hIL-1ε       NLVAVPRSDSVT---PVTVAVITCKYPEALEQGRGDPIYLGIQ-NPEMCL    86
mIL-1δ       QLLAGGLHAEKVIK-GEEISVVPNRALDA----SLSPVILGVQ-GGSQCL
hIL-1δ       QLLAGGLHAGKVIK-GEEISVVPNRWLDA----SLSPVILGVQ-GGSQCL    68 hIL-1α       TAQD--EDQPVLLKEMPEIPKTI-TGSETNLLFFWETHG---TKNYFTSV
hIL-1β       SCVLKDDKPTLQLESVDPKNYP-KKKMEKRFVFNKIEIN---NKLEFESA
hIL-1RA      SCVKSGDETRLQLEAVNITDLSENRKQDKRFAFIRSDSG---PTTSFESA
mIL-1γ       SCKN----KIISFEEMDPPENI--DDIQSDLIFFQKRVPGH-NKMEFESS
hIL-1γ       SCEN----KIISFKEMNPPDNI--KDTKSDIIFFQRSVPGHDNKMQFESS
mIL-1ε       FCTKDGEQPVLQLGEGNIMEMYNKKEPVKASLFYHKKSG---TTSTFESA
hIL-1ε       YCEKVGEQPTLQLKEQKIMDLYGQPEPVKPFLFYRAKTG---RTSTLESV   133
mIL-1δ       SCGT-EKGPILKLEPVNIMELYLGAKESKSFTFYRRDMG---LTSSFESA
hIL-1δ       SCGV-GQEPTLTLEPVNIMELYLGAKESKSFTFYRRDMG---LTSSFESA   114 hIL-1α       AHPNLFIATKQD---YWVCLAG------GPPSITDFQILENQA
hIL-1β       QFPNWYISTSQA-ENMPVFLGGTK----GGQDITDFTMQFVSS
hIL-1RA      ACPGWFLCTAMEAD-QPVSLTNMPDEG---VMVTKFYFQEDE
mIL-1γ       LYEGHFLACQKEDDAFKLILKKKDE---NGDKSVMFTLTNLHQS
hIL-1γ       SYEGYFLACEKERDLFKLILKKEDE---LGDRSIMFTVQNED
mIL-1ε       AFPGWFIAVCSKG-SCPLILTQELG----EIFITDFEMIVVH
hIL-1ε       AFPDWFIASSKRD--QPIILTSELG----KSYNTAFELNIND   169
mIL-1δ       AYPGWFLCTSPEAD-QPVRLTQIPEDPAWDAPITDFYFQQCD
hIL-1δ       AYPGWFLCTVPEAD-QPVRLTQLPENGGWNAPITDFYFQQCD   155
```

FIG. 1

MAMMALIAN CYTOKINES; RECEPTORS; RELATED REAGENTS AND METHODS

This filing is a U.S. Utility Patent Application, which claims the benefit of filing of U.S. Provisional Patent Application, U.S. Ser. No. 60/179,638, filed Feb. 2, 2000.

FIELD OF THE INVENTION

The present invention relates to compositions and methods for affecting mammalian physiology, including morphogenesis or immune system function. In particular, it provides nucleic acids, proteins, and antibodies which regulate development and/or the immune system; and provides functional details on ligand-receptor pairing. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotent hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

The interleukin-1 family of proteins includes the IL-1α, the IL-1β, the IL-1RA (IL-1 receptor antagonist), and recently the IL-1γ (also designated Interferon-Gamma Inducing Factor, IGIF). This related family of genes have been implicated in a broad range of biological functions, e.g., inflammatory, infectious, or other immunological responses. See Dinarello (1994) FASEB J. 8:1314–1325; Dinarello (1991) Blood 77:1627–1652; and Okamura, et al. (1995) Nature 378:88–91.

In addition, various growth and regulatory factors exist which modulate morphogenetic development. This includes, e.g., the Toll ligands, which signal through binding to receptors which share structural, and mechanistic, features characteristic of the IL-1 receptors. See, e.g., Lemaitre, et al. (1996) Cell 86:973–983; and Belvin and Anderson (1996) Ann. Rev. Cell&Develop. Biol. 12:393–416.

From the foregoing, it is evident that the discovery and development of new soluble proteins, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel lymphokine-like molecules which enhance or potentiate the beneficial activities of other lymphokines would be highly advantageous. The present invention provides new interleukin-1 like compositions and related compounds, and methods for their use.

BRIEF DESCRIPTION OF THE DRAWINGS

FIG. 1 shows an alignment between various IL-1 family members. Positions re er to the alignment and are not residue numbers. hIL-1α is SEQ ID NO:5; hIL-1β is SEQ ID NO:6; hIL-1RA is is SEQ ID NO:7; mIL-1γ is SEQ ID NO:8; hIL-1γ is SEQ ID NO:9; mIL-1ε is SEQ ID NO:10; hIL-1ε is SEQ ID NO:4; mIL-1ε is SEQ ID NO:11; and hIL-1δ is SEQ ID NO:2.

SUMMARY OF THE INVENTION

The present invention is based on the discovery, purification, and characterization of the biological activities of novel interleukin-1 like molecules, designated interleukin-1δ (IL-1δ) and interleukin-1ε (IL-1ε). IL-1δ and IL-L1δ exhibit both structural and sequence similarity, e.g., by homology comparison, to known members of the IL-1 family of molecules. In addition, part of the receptor for these molecules has been defined, the IL-1R related protein 2 (also designated or IL-1R6), and the two molecules are agonist (IL-1ε) and antagonist (IL-1δ). Thus, the receptor/ligand matching provides a similar family to the IL-1α/IL-1β/IL-1RA signaling system.

The present invention provides various methods of producing a ligand:receptor complex, comprising contacting: a substantially pure or recombinant mammalian IL-1δ or IL-1ε with a receptor comprising the IL-1R6 receptor subunit; or a mammalian IL-1δ or IL-1ε with a receptor comprising a substantially pure or recombinant IL-1R6 receptor subunit; thereby allowing the complex to form. Such methods include those in which: the complex results in modulation of NFκB activation; the receptor is on a cell; the complex formation results in a physiological change in the cell expressing the receptor; the contacting is in combination with an anti-inflammatory agent; or the contacting allows quantitative detection of the ligand. In other methods, the receptor is on a skin cell.

Other methods include methods of modulating physiology or development of an IL-1R6 receptor expressing cell comprising contacting the cell to an exogenous agonist or antagonist of a mammalian IL-1δ or IL-1ε. In some embodiments: the antagonist is: an antibody which: neutralizes the mammalian IL-1δ; or neutralizes the mammalian IL-1ε; or a mutein of the IL-1δ or IL-1ε; or the physiology is selected from: proliferation; tissue remodeling; or production of inflammatory mediators, including cytokines, chemokines, or adhesion molecules; or the modulating is specific for epithelial cells and not endothelial cells. In other embodiments, the antagonist is an antibody and the physiology is an inflammatory response; the modulating is specific for Th2 cells and not Th1 cells; or the modulating is blocking, and the physiology is an inflammatory response.

Other aspects of the invention provide methods of modulating a signal to a cell mediated by IL-1δ or IL-1ε comprising contacting the cell to an administered agonist or antagonist of IL-1R6. In some forms, the modulating is inhibiting, and the signal is a pro-inflammatory signal; or the antagonist is a neutralizing antibody to IL-1R6; the agonist or antagonist is administered in combination with an antagonist or agonist of CXCR1, CXCR2, or CCR6; or the agonist or antagonist is administered in combination with a growth factor, cytokine, chemokine, or immune adjuvant. Certain combinations include contacting with another anti-inflammatory agent.

Other methods include selectively labeling a population of cells, the method comprising contacting the cells with an IL-1R6 antibody or a cytokine selected from IL-1δ or IL-1ε, thereby resulting in the identification of cells expressing IL-1R6. Preferably, the contacting results in modulation of NFκB activation; the labeling allows purification of IL-1R6+ cells; or the labeling allows depletion of IL-1R6+ cells. Such methods also alow preparation of a population of cells, e.g., which: bind anti-IL-1R6 antibody or antiserum; or are prepared by Fluorescent Activated Cell Sorting with a labeled IL-1R6 selective: ligand; antibody; or binding compound comprising the antigen binding portion from an antibody which selectively binds IL-1R6.

The invention also provides means to test a compound for ability to affect IL-1R6 receptor-ligand interaction, the method comprising comparing the interaction of IL-1R6 with IL-1δ or IL-1ε in the presence and absence of the compound. In some forms, the compound is an antibody against IL-1R6, IL-1δ, or IL-1ε.

Compositions are also provided based upon the sequences provided herein, e.g., an isolated or recombinant polynucleotide which: encodes at least 15 contiguous amino acid residues of SEQ ID NO: 2; encodes at least two distinct segments of at least 8 contiguous amino acid residues of SEQ ID NO 2; comprises one or more segments at least 21 contiguous nucleotides of SEQ ID NO: 1; encodes at least 15 contiguous amino acid residues of SEQ ID NO: 4; encodes at least two distinct segments of at least 8 contiguous amino acid residues of SEQ ID NO 4; or comprises one or more segments at least 21 contiguous nucleotides of SEQ ID NO: 3. Polypeptide embodiments are provided, e.g., an isolated or recombinant antigenic polypeptide comprising at least: one segment of 12 identical contiguous amino acids from SEQ ID NO: 2; at least two distinct segments of 8 identical contiguous amino acids from SEQ ID NO: 2; one segment of 12 identical contiguous amino acids from SEQ ID NO: 4; or at least two distinct segments of 8 identical contiguous amino acids from SEQ ID NO: 4. Binding compositions are also provided, e.g., binding compound comprising an antigen binding portion from an antibody which binds with selectivity to the polypeptides.

DETAILED DESCRIPTION OF THE PREFERRED EMBODIMENTS

OUTLINE

| | |
|---|---|
| I. | General |
| II. | Activities |
| III. | Nucleic acids |
| | A. encoding fragments, sequence, probes |
| | B. mutations, chimeras, fusions |
| | C. making nucleic acids |
| | D. vectors, cells comprising |
| IV. | Proteins, Peptides |
| | A. fragments, sequence, immunogens, antigens |
| | B. muteins |
| | C. agonists/antagonists, functional equivalents |
| | D. making proteins |
| V. | Making nucleic acids, proteins |
| VI. | Antibodies |
| | A. polyclonals |
| | B. monoclonal, Kd |
| | C. anti-idiotypic antibodies |
| | D. hybridoma cell lines |
| VII. | Kits and Methods to quantify IL-1δ |
| | A. ELISA |
| | B. assay mRNA encoding |
| | C. qualitative/quantitative |
| | D. kits |
| VIII. | Therapeutic compositions, methods |
| | A. combination compositions |
| | B. unit dose |
| | C. administration |
| IX. | Receptors |

I. General

Before the present compositions, formulations, and methods are described, it is to be understood that this invention is not limited to the particular methods, compositions, and cell lines described herein, as such methods, compositions, and cell lines may, of course, vary. It is also to be understood that the terminology used herein is for the purpose of describing particular embodiments.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. Publications, patent applications, patents, and other references discussed above are provided solely for their disclosure prior to the filing date of the present application. Nothing herein is to be construed as an admission that the invention is not entitled to antedate any such disclosure by virtue of its prior invention. Publications, patent applications, patents, and other references mentioned herein are incorporated by reference in their entirety including all figures and drawings.

The present invention provides the amino acid sequence and DNA sequence of primate, e.g., human, interleukin-1 like molecule having particular defined properties, both structural and biological. These have been designated herein as interleukin-1δ (IL-1δ). Non-human primate counterparts should also exist, since rodents possess a counterpart. The nucleic acids encompassed herein include DNA, cDNA, and RNA sequences which encode IL-1δ. It is understood that nucleic acids encoding all or a portion of the primate IL-1δ polypeptides are also encompassed. Such nucleic acids include both naturally occurring and intentionally manipulated nucleic acids. For example, IL-1δ may be subjected to site-directed mutagenesis.

IL-1 family members are known to alter the host response to an inflammatory, infectious or immunological challenge. Dinarello (1994) *Eur. Cytokine Netw.* 5:517–531. IL-1s are in fact 'primary' cytokines as IL-1s are capable of inducing and orchestrating inflammation. IL-1 activity, therefore, is tightly controlled under physiological conditions. The classical IL-1 family comprises several ligands (e.g., IL-1α, IL-1β, and IL-1 receptor antagonist (IL-1RA) (March, et al. (1985) *Nature* 315:641–647; Hannum, et al. (1990) *Nature* 343:336–340; and Eisenberg, et al. (1990) *Nature* 343:341–346), and surface and soluble IL-1 receptors (IL-1RI, RII, and IL-1R accessory proteins designated IL-1R1, 2, and 3 herein, respectively; see, Sims, et al. (1988) *Science* 241:585–589; McMahan, et al. (1991) *EMBO J.* 10:2821–2832; and Greenfeder, et al. (1995) *J. Biol. Chem.* 270:13757–13765, in keeping with the previously proposed numbering system, as in Rock, et al. (1998) *Proc. Nat'l Acad. Sci. USA* 95:588–593). IL-1 signaling is initiated by high-affinity binding of IL-1α/β to IL-1R1, which gets subsequently bound by R3 (Sims, et al. (1988) *Science* 241:585–589; and Greenfeder, et al. (1995) *J. Biol. Chem.* 270:13757–13765). This results in an intracellular signaling cascade quite similar to stress-induced signal transduction (Freshney, et al. (1994) *Cell* 78:1039–1049), with the end effect being NFκB activation (O'Neill and Greene (1998) *J. Leukoc. Biol.* 63:650–657). IL-1 signaling is unusually efficient, as only one to ten IL-1 molecules bound per cell are required to trigger an IL-1 response. Nature designed specific 'roadblocks' to reduce the IL-1 response when necessary. In addition to controlling gene expression, synthesis and secretion, this regulation extends to antagonists of the IL-1 response. IL-1RA and IL-1R2 antagonize the response to IL-1α/β at the receptor and ligand level, respectively. Hannum, et al. (1990) *Nature* 343:336–340; Eisenberg, et al. (1990) *Nature* 343:341–346; and Colotta, et al. (1994) *Immunol. Today* 15:562–566). Numerous studies have shown that perturbation of such control contributes to the pathogenesis of inflammatory and immunological diseases (e.g., leukemias, rheumatoid arthritis, and psoriasis). Dinarello (1996) *Blood* 87:2095–2147.

Recently, additional members were added to the IL-1 family based on sequence homology and the presence of key structural patterns. For example, IL-18 (IL-1γ; Okamura, et al. (1995) *Nature* 378:88–91; Ushio, et al. (1996) *J. Immunol.* 156:4274–4279) is predicted to fold as a β-rich trefoil, typical for IL-1 ligands (Bazan, et al. (1996) *Nature* 379:591). Moreover, with respect to processing, receptor usage and signaling, IL-18/IL-1γ can be classified as an IL-1 family member. Ghayur, et al. (1997) *Nature* 386:619–623; Gu, et al. (1997) *Science* 275:206–209; Torigoe, et al. (1997) *J. Biol. Chem.* 272:25737–25742; Born, et al. (1998) *J. Biol. Chem.* 273:29445–29450; Robinson, et al. (1997) *Immunity.* 7:571–581; and Kojima, et al. (1998) *Biochem. Biophys. Res. Commun.* 244:183–186. Also at the receptor level, additional IL-1R-like molecules exist, many of which are currently orphan receptors, such as T1/ST2 (termed IL-1R4; Klemenz, et al. (1989) *Proc. Nat'l Acad. Sci. USA* 86:5708–5712; and Tominaga (1989) *FEBS Lett.* 258:301–304), IL-1Rrp1 (IL-1R related protein 1; IL-1R5; Parnet et al. (1996) *J. Biol. Chem.* 271:3967–3970) and IL-1R related protein 2 (IL-1R6; Lovenberg, et al. (1996) *J. Neuroimmunol.* 70:113–122), IL-1RacPL (IL-1R7; Born, et al. (1998) *J. Biol. Chem.* 273:29445–29450), single Ig domain IL-1R-related protein (SIGIRR, e.g., IL-1R8; Thomassen, et al. (1999) *Cytokine* 11:389–399), IL-1R accessory protein-like (IL-1RAPL; IL-1R9; Carrie, et al. (1999) *Nat. Genet.* 23:25–31), and IL-1R10 (Sana, T. R., R. Debets, J. C. Timans, J. F. Bazan, and R. A. Kastelein: submitted for publication), all harboring extracellular Ig-folds and an intracellular domain homologous to the cytosolic part of the Drosophila Toll protein. It is interesting to note that the majority of the IL-1 ligands (e.g., IL-1α/β/ra) and IL-1Rs (e.g., IL-1R1, 2, 4, 5, 6, and 7) are clustered and localized to Chr. 2 (Born, et al. (1998) *J. Biol. Chem.* 273:29445–29450; Lafage, et al. (1989) *Blood* 73:104–107; Patterson, et al. (1993) *Genomics* 15:173–176; Sims, et al. (1995) *Cytokine* 7:483–490; and Dale and Nicklin (1999) *Genomics* 57:177–179.

The availability of several orphan IL-1Rs points to the existence of other IL-1 ligands. Two novel IL-1 ligands were identified, based on homology with IL-1RA, which have been designated IL-1δ and IL-1ε. These novel IL-1s are strongly expressed in embryonic tissue and epithelial cells, such as skin keratinocytes. Adenovirally-derived human IL-1δ and IL-1ε proteins do not activate NFκB through the classical IL-1Rs, e.g., the IL-1Rs used by IL-1α/β or IL-18. Instead, IL-1ε activates this transcription factor via IL-1R6 and this response is potently and specifically antagonized by IL-1δ.

The expression of IL-1ε, and to a lesser extent of IL-1δ, is significantly upregulated in IL-1β/TNFα-stimulated human keratinocytes. Human IL-1δ and IL-1ε proteins do not activate NFκB through the classical IL-1Rs, i.e., the IL-1Rs used by IL-1α/β (IL-1R1 and IL-1R3) or IL-18 (IL-1R5/IL-1R7). Instead, IL-1ε activates this transcription factor via IL-1R6 and this response is potently and specifically antagonized by IL-1ε. Lesional psoriasis skin shows a substantially increased expression of both the IL-1 ligands as well as their IL-1R. IL-1δ/ε and IL-1R6 probably constitute an independent signaling system, present in epithelial barriers of the body, which may take part in local inflammatory responses.

Some of the standard methods applicable are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al.

(1987 and periodic supplements) *Current Protocols in Molecular Biology*, Greene/Wiley, New York; each of which is incorporated herein by reference. See also U.S. Ser. No. 09/130,972, which is incorporated herein by reference.

A complete nucleotide and corresponding amino acid sequence of a primate, e.g., human, IL-1δ coding segment is shown in SEQ ID NO: 1 and 2. Nucleic and amino acid sequences of IL-1ε are shown in SEQ ID NO:3, 4, and 10 (human and rodent. FIG. 1 shows an alignment of selected family members.

For the primate, e.g., human, IL-1δ, the beta sheet regions run from about leu7-met11; val18-leu21; leu26-gly29; ile42-asn47; pro56-val61; gln66-gly71; thr77-pro82; phe98-arg103; ser110-ser113; trp119-thr123; pro130-thr134; and pro145-gln153. Site A residues correspond to about lys12; ser14-leu16; leu21-asn23; leu27; gly29-gly34; val36; lys38; pro125-glu126; asp128-pro130; tyr150, and gln152. Site B residues correspond to about met1-gly5; leu7; asn47; trp49; ser53; ser55; gly91-lys93; arg102; asp104-met105; leu107-thr108; gln153; and asp155. Asp148 corresponds to a residue which is particularly important in the IL-1RA.

For the primate, e.g., human, IL-1ε, the beta sheet regions run from about ile23-ile27; val34-thr36; leu42-val45; val56-cys61; pro74-ile79; met84-glu89; thr96-glu101; phe117-ala122; thr129-ser132; trp138-ser142; pro148-thr152; and tyr159-ile167. Site A residues correspond to about asn28; leu30-gln32; thr36-gln38; val43; val45-ser50; thr52; lys144-arg145; gln147-pro148; glu164; and asn166. Site B residues correspond to about gln17-cys20; ile23; cys61; tyr63; glu68; gly70-arg71; asp73; gln110-glu112; arg121; lys123-thr124; arg126-thr127; ile167; and asp169. Ala162 corresponds to a residue which is particularly important in the IL-1RA.

Segments with boundaries adjacent these positions will be particularly useful. Mutagenesis in these regions will be used to determine structure-activity relationship, particularly with the receptor, as provided herein.

Complete nucleotide and corresponding amino acid sequences of mammalian, e.g., primate and rodent, e.g., human and mouse, IL-1R6 coding segments are shown SEQ ID Nos:12, 13, 14, and 15.

As used herein, the term "primate IL-1δ" shall be used to describe a protein comprising a protein or peptide segment having or sharing the amino acid sequence shown in SEQ ID NO:2, or a substantial fragment thereof; but distinct from rodent sequences. The invention also includes protein variations of the IL-1δ allele whose sequence is provided, e.g., a mutein agonist or antagonist. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic variants, of the protein described. "Natural" as used herein means unmodified by artifice, found, e.g., in natural sources. Typically, it will bind to its corresponding biological receptor with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the primate protein.

This invention also encompasses proteins or peptides having substantial amino acid sequence homology with the amino acid sequence in SEQ ID NO:2. It will include sequence variants with relatively few substitutions, e.g., preferably less than about 3–5.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches.

Amino acid sequence homology, or sequence identity, is determined by optimizing residue matches, if necessary, by introducing gaps as required. See, e.g., Needleham, et al., (1970) *J. Mol. Biol.* 48:443–453; Sankoff, et al., (1983) chapter one in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50–100% homology (if gaps can be introduced), to 60–100% homology (if conservative substitutions are included) with an amino acid sequence segments of SEQ ID NO:2 or 4. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described in SEQ ID NO:2. As used herein, the term "biological activity" is used to describe, without limitation, effects on inflammatory responses and/or innate immunity. For example, they may, like IL-1γ, exhibit synergistic induction by splenocytes of IFN-γ in combination with IL-12 or IL-2, with or without anti-type I or anti-type II IL-1 receptor antibodies, or more structural properties as receptor binding and cross-reactivity with antibodies raised against the same or a polymorphic variant of a mammalian IL-1δ.

The terms ligand, agonist, antagonist, and analog of IL-1δ include molecules that modulate the characteristic cellular responses to IL-1δ or IL-1δ-like proteins, as well as molecules possessing the more standard structural binding competition features of ligand-receptor interactions, e.g., where the receptor is a natural receptor or an antibody. The cellular responses likely are mediated through binding of IL-1δ to cellular receptors related to, but possibly distinct from, the type I or type II IL-1 receptors. Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds.) (1990) *Goodman&Gilman's: The Pharmacological Bases of Therapeutics*, Pergamon Press, New York.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

II. Activities

The IL-1δ proteins will have a number of different biological activities, e.g., in the immune system, and will include inflammatory functions or disorders, e.g., psoriasis, or other innate immunity responses. The IL-1δ or IL-1ε proteins are homologous to other IL-1 proteins, but each have structural differences. For example, a human IL-1γ gene coding sequence probably has about 70% identity with the nucleotide coding sequence of mouse IL-1γ, and similar measures of similarity will apply to the IL-1δ and IL-1ε. At the amino acid level, there is also likely to be about 60% identity. This level of similarity suggests that the new IL-1δ and IL-1ε proteins are related to the other IL-1α and IL-1β and IL-1RA.

The mouse IL-1γ molecule has the ability to stimulate IFN-γ production which augments NK activity in spleen cells. See Okamura, et al. (1995) *Nature* 378:88–91.

The activities of the mouse IL-1α, IL-1β, and IL-1γ have been compared as to their ability to induce IFN-γ, alone or in combination with IL-2 or IL-12 in SCID splenocytes and purified NK cells. See Hunter, et al. (1995) *J. Immunol.* 155:4347–4354; and Bancroft, et al. (1991) *Immunol. Revs.* 124:5–24. The IL-1γ was found to be much more potent in stimulating IFN-1γ than either IL-1α or IL-1β. IL-1δ and IL-1ε and their agonists or antagonists should have related activities, typically affecting similar immune functions, including inflammatory responses.

In IL-2 activated NK cells, IFN-γ production is blocked by the addition of anti-IL-1β antibodies. See Hunter, et al. (1995). However, mouse IL-1γ can overcome this block and induce IFN-γ. This is the only cytokine known to be able to do this. In addition, in vivo, administration of mouse IL-1γ to mice infected with the parasite T. Cruzi significantly decreases parasitemia. IL-1δ and IL-1ε and their agonists or antagonists should operate through related mechanisms and effectors.

The present disclosure also describes new assays for activities predicted for the IL-1δ and IL-1ε molecules. Corresponding activities should be found in other mammalian systems, including primates. It is likely that the new IL-1-like molecules produced by similar recombinant means to the human IL-1γ protein should exhibit a biological activity of modulating lymphocyte cells in production of IFN-γ. See assays described, e.g., in de Waal Malefyt, et al., in de Vries and de Waal Malefyt (eds. 1995) "Interleukin-10" Landes Co., Austin, Tex. Furthermore, there is substantial likelihood of synergy with other IL-1 or IL-12 related agonists or antagonists. It is likely that the receptors, which are expected to include multiple different polypeptide chains, exhibit species specificity for their corresponding ligands. The IL-1α and IL-1β ligands both signal through heterodimeric receptors.

III. Nucleic Acids

This invention contemplates use of isolated nucleic acid or fragments, e.g., which encode this or a closely related protein, or fragments thereof, e.g., to encode a biologically active corresponding polypeptide.

The term "isolated nucleic acid or fragments" as used herein means a nucleic acid, e.g., a DNA or RNA molecule, that is not immediately contiguous with sequences present in the naturally occurring genome of the organism from which it is derived. Thus, the term describes, e.g., a nucleic acid that is incorporated into a vector, such as a plasmid or viral vector; a nucleic acid that is incorporated into the genome of a heterologous cell (or the genome of homologous cell, but at a site different from that at which it normally occurs); and a nucleic acid that exists as a separate molecule, e.g., a DNA fragment produced by PCR amplification or restriction enzyme digestion, or an RNA molecule produced by in vitro transcription. The term also describes a recombinant (e.g., genetically engineered) nucleic acid that forms part of a hybrid gene encoding additional polypeptide sequences that can be used, e.g., in the production of a fusion protein. In addition, this invention embodies any engineered or nucleic acid molecule created by artifice that encodes a biologically active protein or polypeptide having characteristic IL-1δ or IL-1ε activity. Typically, the nucleic acid is capable of hybridizing, under appropriate conditions, with a nucleic acid sequence segment shown in SEQ ID NO:1. Further, this invention covers the use of isolated or recombinant nucleic acid, or fragments thereof, which encode proteins having fragments which are homologous to the newly disclosed IL-1-like proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, e.g., products made by transforming cells with any unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode similar polypeptides to fragments of the IL-1δ or IL-1ε and fusions of sequences from various different interleukin or related molecules, e.g., growth factors.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides; usually at least 60 nucleotides, more usually at least 66 nucleotides, preferably at least 72 nucleotides, more preferably at least 79 nucleotides, and in particularly preferred embodiments will be at least 85 or more nucleotides including, e.g., 100, 150, 200, 250, etc. Typically, fragments of different genetic sequences can be compared to one another over appropriate length stretches, particularly defined segments such as the domains described below.

A nucleic acid which codes for an IL-1δ will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth, herein. In particular, the sequences will often be operably linked to DNA segments which control transcription, translation, and DNA replication. These additional segments typically assist in expression of the desired nucleic acid segment.

Homologous nucleic acid sequences, when compared to one another or SEQ ID NO:1 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from SEQ ID NO:1 or 3. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nuc. Acids Res.* 12:203–213. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. Certain detergents or destabilizing reagents may be added, e.g., formamide at 50%, etc. However, the combination of parameters is much more important than the measure of any single parameter. See, e.g., Wetmur and Davidson (1968) *J. Mol. Biol.* 31:349–370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant IL-1-like derivatives include predetermined or site-specific mutations of the protein or its fragments, including silent mutations using genetic code degeneracy. "Mutant IL-1δ" as used herein encompasses a polypeptide otherwise falling within the homology definition of the IL-1δ as set forth above, but having an amino acid sequence which differs from that of other IL-1-like proteins as found in nature, whether by way of deletion, substitution, or insertion. In particular, "site specific mutant IL-1δ" encompasses a protein having substantial homology with a protein of SEQ ID NO:2, and typically shares most of the biological activities of the form disclosed herein.

Although site specific mutation sites are predetermined, mutants need not be site specific. Mammalian IL-1δ mutagenesis can be achieved by making amino acid insertions or deletions in the gene, coupled with expression. Substitutions, deletions, insertions, or any combinations may be generated to arrive at a final construct. Insertions include amino- or carboxy- terminal fusions. Random mutagenesis can be conducted at a target codon and the expressed mammalian IL-1δ mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (eds. 1995) *PCR Primer: A Laboratory Manual* Cold Spring Harbor Press, CSH, NY.

IV. Proteins, Peptides

As described above, the present invention encompasses primate IL-1δ, e.g., whose sequences are disclosed in SEQ ID NO:2, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these rodent proteins. A heterologous fusion protein is a fusion of proteins or segments which are naturally not normally fused in the same manner. Thus, the fusion product of a growth factor with an interleukin is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional or structural domains from other related proteins, e.g., growth factors or other cytokines. For example, receptor-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of receptor-binding specificities. For example, the receptor binding domains from other related ligand molecules may be added or substituted for other domains of this or related proteins. The resulting protein will often have hybrid function and properties. For example, a fusion protein may include a targeting domain which may serve to provide sequestering of the fusion protein to a particular organ, e.g., a ligand portions which is specifically bound by spleen cells and would serve to accumulate in the spleen.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

The present invention particularly provides muteins which act as agonists or antagonists of the IL-1δ. Structural alignment of IL-1δ and IL-1ε with other members of the IL-1 family show conserved features/residues, particularly 12 β strands folded into a β-trefoil fold.

Alignment of the IL-1δ and IL-1ε sequences with other members of the IL-1 family indicates that the β conformations correspond to similar sequences in other IL-1 family members. See FIG. 1 and, e.g., Bazan, et al. (1996) *Nature* 379:591; Lodi, et al. (1994) *Science* 263:1762–1766; Sayle and Milner-White (1995) *TIBS* 20:374–376; and Gronenberg, et al. (1991) *Protein Engineering* 4:263–269.

The IL-1α and IL-1β ligands bind an IL-1 receptor type I as the primary receptor and this complex then forms a high affinity receptor complex with the IL-1 receptor type III. Such receptor subunits are probably shared with the new IL-1 family members.

The mouse IL-1γ does not bind to the known mouse IL-1 receptor types I, II (decoy receptor), or III. In addition, the mouse IGIF biological activity cannot be blocked with anti-type I, II, or III antibodies. This suggests that the related mouse IGIF binds to receptors related to the IL-1 receptors already isolated, e.g., IL-1R related proteins 1 (IL-1Rrp1) and IL-RAcPL.

The solved structures for IL-1β, the natural IL-1 receptor antagonist (IL-1Ra), and a co-structure of IL-1Ra/IL-1 receptor type I, however, suggest how to make an IL-1δ or IL-1ε antagonist. See, e.g., accession numbers: U65590, gbU19844, gbU19845, gi2173679, gi2170133, gi2172939, gbM15300, gbM28983, gbU65590, gbM74294, embX04964, gi2169698, gi2169368 emb270047, gi914939, gi220782, embX52731, embX56972 and embX12497, for various species examples of IL-1 family members. Structural analyses of the mature IL-1δ or IL-1ε suggest that its β-trefoil structures contact the IL-1 receptor over three binding sites (designated A, B, and C). Sites A and C bind to the first receptor subunit (alpha) of IL-1 while site B binds the IL-1 second receptor subunit (beta). Homology sequence comparison of the IL-1 family members reveals that the only known antagonist to IL-1 receptor (IL-1ra; FIG. 1) is missing an amino acid domain bounded by the β4 and β5 strands. This domain maps to a portion of site B in rodent IL-1δ or IL-1ε (FIG. 1) that binds to the IL-1 second receptor subunit, suggesting that its absence confers antagonist activity as evidenced by homology comparison among other IL-1 family members. This loop portion of contact site B spans approximately 7–10 amino acid residues, while in IL-1RA the loop is "cut off" with only 2 residues remaining. Therefore, IL-1RA binds normally to receptor type I, but cannot interact with receptor type III. This makes IL-1RA into an effective IL-1 antagonist.

The corresponding location in rodent IL-1δ or IL-1ε (between β4 and β5) defines a domain that forms a polypeptide loop which is part of a primary binding segment to the IL-1 receptor type (site B). With mouse IL-1RA, it was shown that replacement of the mouse IL-1RA residues with those mouse IL-1β residues introduced IL-1 activity to the IL-1RA variant(IL-1RA could then bind type III receptor). Similar substitutions should establish that type III receptor can probably be used by mouse IL-1δ or IL-1ε proteins or muteins.

Sites A and C mediate binding of IL-1δ or IL-1ε to the first IL-1 receptor subunit, e.g., an alpha receptor subunit. Site A contacts correspond in primate IL-1δ to amino acid residues 12, 14–16, 21–23, 27, 29–34, 36, 38, 125–126, 128–130; 150, and 152 of SEQ ID NO: 2; while site C contacts correspond in primate IL-1δ to amino acid residues 73–97 of SEQ ID NO: 2. Site B contacts are defined in primate IL-1δ by amino acid residues 1–5, 7, 47, 49, 53, 55, 91–93, 102r 104–105, 107–108, 153, and 155. Site A contacts correspond in primate IL-1ε to amino acid residues 28, 30–32, 36–38, 43, 45–50, 52, 144–145, 147–148, 164, and 166 of SEQ ID NO: 13; while site C contacts correspond in primate IL-1ε to amino acid residues 73–97 of SEQ ID NO: 4. Site B contacts are defined in primate IL-1ε by amino acid residues 17–20, 23, 61, 63, 68, 70–7:1, 73, 110–112, 121, 123–124, 126–127, 167, and 169 of SEQ ID NO: 4.

Similar variations in other species counterparts of IL-1δ ligand sequence, e.g., in the corresponding regions, should provide similar interactions with receptor. Substitutions with either mouse sequences or human sequences are indicated. Conversely, conservative substitutions away from the receptor binding interaction regions will probably preserve most biological activities.

"Derivatives" of the mammalian IL-1δ include amino acid sequence mutants, glycosylation variants, metabolic derivatives and covalent or aggregative conjugates with other chemical moieties. Covalent derivatives can be prepared by linkage of functionality's to groups which are found in the IL-1δ amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the interleukin or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the interleukin and other homologous or heterologous proteins are also provided. Homologous polypeptides may be fusions between different growth factors, resulting in, for instance, a hybrid protein exhibiting ligand specificity for multiple different receptors, or a ligand which may have broadened or weakened specificity of binding to its receptor. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, yeast alpha mating factor, or other cytokines, e.g., IL-1 family members. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), Vols. 1–3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference. See also Dawson, et al. (1994) *Science* 266:776–779 for methods to make larger polypeptides.

In another embodiment, the present invention relates to substantially purified peptide fragments of IL-1δ or IL-1ε that block binding between IL-1 family members and a target receptor. Such peptide fragments could represent research and diagnostic tools in the study of inflammatory reactions to antigenic challenge and the development of more effective anti-inflammatory therapeutics. In addition, pharmaceutical compositions comprising isolated and purified peptide fragments of IL-1δ or IL-1ε may represent effective anti-inflammatory therapeutics.

The term "substantially purified" as used herein refers to a molecule, such as a peptide that is substantially free of other proteins, lipids, carbohydrates, nucleic acids, or other biological materials with which it is naturally associated. For example, a substantially pure molecule, such as a polypeptide, can be at least 60%, by dry weight, the molecule of interest. One skilled in the art can purify IL-1δ or IL-1ε peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The invention relates not only to fragments of naturally-occurring IL-1δ or IL-1ε, but also to IL-1δ or IL-1ε mutants and chemically synthesized derivatives of IL-1δ or IL-1ε that block binding between IL-1 family members and a target receptor.

For example, changes in the amino acid sequence of IL-1δ or IL-1ε are contemplated in the present invention. IL-1δ or IL-1ε can be altered by changing the nucleic acid sequence encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of IL-1δ or IL-1ε can be used in the present invention. Variants include analogs, homologues, derivatives, muteins, and mimetics of IL-1δ or IL-L1ε that retain the ability to block binding between IL-1 family members and a target receptor. Fragments of the IL-1δ or IL-1ε refer to portions of the amino acid sequence of IL-1δ or IL-1ε as defined in SEQ ID NO: 2 or 4 that also retain this ability. The variants and fragments can be generated directly from IL-1δ or IL-1ε itself by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of IL-1δ or IL-1ε ("mimetics") can be produced by the approach outlined in Saragovi, et al. (1991) *Science* 253:792–95. Mimetics are molecules which mimic elements of protein secondary structure. See, e.g., Johnson et al., "Peptide Turn Mimetics," in Pezzuto, et al. (eds. 1993) *Biotechnology and Pharmacy*, Chapman and Hall, New York. The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of IL-1δ or IL-1ε itself.

Variants and fragments also can be created by recombinant techniques employing genomic or cDNA cloning methods. Site-specific and region-directed mutagenesis techniques can be employed. See, e.g., vol. 1, ch. 8 in Ausubel, et al. (eds. 1989 and periodic updates) *Current Protocols in Molecular Biology* Wiley and Sons; and Oxender and Fox (eds.) *Protein Engineering* Liss, Inc. In addition, linker-scanning and PCR-mediated techniques can be employed for mutagenesis. See, e.g., Erlich (ed. 1989) *PCR Technology* Stockton Press. Protein sequencing, structure and modeling approaches for use with any of the above techniques are disclosed, e.g., in Oxender and Fox (eds.) *Protein Engineering* Liss, Inc; and Ausubel, et al. (eds. 1989 and periodic updates) *Current Protocols in Molecular Biology* Wiley and Sons.

This invention also contemplates the use of derivatives of IL-1δ other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, e.g., with cell membranes. Such covalent or aggregative derivatives are useful as immunogens, as reagents in immunoassays, or in purification methods such as for affinity purification of a receptor or other binding molecule, e.g., an antibody. For example, an IL-1δ ligand can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of IL-1δ receptor, antibodies, or other similar molecules. The IL-1δ can also be labeled with a detectable group, e.g., radio-iodinated by the chloramine T procedure, covalently bound to rare earth chelates, or conjugated to another fluorescent moiety for use in diagnostic assays.

An IL-1δ of this invention can be used as an immunogen for the production of antisera or antibodies specific, e.g., capable of distinguishing between other IL-1 family members and an IL-1δ, for the interleukin or any fragments thereof. The purified interleukin can be used to screen monoclonal antibodies or antigen-binding fragments prepared by immunization with various forms of impure preparations containing the protein. In particular, the term "antibodies" also encompasses antigen binding fragments of natural antibodies. The purified interleukin can also be used as a reagent to detect any antibodies generated in response to the presence of elevated levels of expression, or immunological disorders which lead to antibody production to the endogenous cytokine. Additionally, IL-1δ fragments may also serve as immunogens to produce the antibodies of the present invention, as described immediately below. For example, this invention contemplates antibodies having binding affinity to or being raised against the amino acid sequence shown in SEQ ID NO:2, fragments thereof, or homologous peptides. In particular, this invention contemplates antibodies having binding affinity to, or having been raised against, specific fragments which are predicted to be, or actually are, exposed at the exterior protein surface of the native cytokine.

The blocking of physiological response to these interleukins may result from the inhibition of binding of the ligand to the receptor, likely through competitive inhibition. Thus, in vitro assays of the present invention will often use antibodies or ligand binding segments of these antibodies, or fragments attached to solid phase substrates. These assays will also allow for the diagnostic determination of the effects of either binding region mutations and modifications, or ligand mutations and modifications, e.g., ligand analogs.

This invention also contemplates the use of competitive drug screening assays, e.g., where neutralizing antibodies to the interleukin or fragments compete with a test compound for binding to a receptor or antibody. In this manner, the neutralizing antibodies or fragments can be used to detect the presence of any polypeptide which shares one or more binding sites to a receptor and can also be used to occupy binding sites on a receptor that might otherwise bind an interleukin.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in SEQ ID NO:1. Other species counterparts, e.g., primate, can be identified by hybridization techniques, or by various PCR techniques, combined with or by searching in sequence databases.

This DNA can be expressed in a wide variety of host cells for the synthesis of a full-length interleukin or fragments which can in turn, e.g., be used to generate polyclonal or monoclonal antibodies; for binding studies; for construction and expression of modified agonist/antagonist molecules; and for structure/function studies. Each variant or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a functionally, e.g., biologically active, equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the interleukin protein or its fragments in various hosts using vectors that do not contain a replication origin that is recognized by the host cell. It is also possible to use vectors that cause integration of the protein encoding portion or its fragments into the host DNA by recombination, e.g., downstream of heterologous promoters.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds) *Vectors: A Survey of Molecular Cloning Vectors and Their Uses*, Buttersworth, Boston, 1988, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the interleukin to accumulate in the culture. The protein can be recovered, either from the culture or from the culture medium.

For purposes of this invention, nucleic acid sequences are operably linked when they are functionally related to each other. For example, DNA for a pre-sequence or secretory leader is operably linked to a polypeptide if it is expressed as a pre-protein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A common vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236, which is incorporated herein by reference.

Lower eukaryotes, e.g., yeasts and Dictyostelium, may be transformed with IL-1δ sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRpseries), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo PolyA, see Thomas, et al. (1987) *Cell* 51:503–512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is typically cleaved prior to secretion of the mature, or active, polypeptide. The cleavage site can be predicted with a high degree of accuracy from empirical rules, e.g., von-Heijne (1986) *Nucleic Acids Research* 14:4683–4690, and the precise amino acid composition of the signal peptide does not appear to be critical to its function. See, e.g., Randall, et al. (1989) *Science* 243:1156–1159; and Kaiser et al. (1987) *Science* 235:312–317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the interleukin gene may be co-transformed with one or more genes encoding mammalian or other glycosylating enzymes. Using this approach, certain mammalian glycosylation patterns will be achievable in prokaryote or other cells.

The source of IL-1δ or IL-1ε can be a eukaryotic or prokaryotic host expressing recombinant IL-1δ or IL-1ε DNA, such as is described above. The source can also be a cell line such as mouse Swiss 3T3 fibroblasts, but other mammalian cell lines are also contemplated by this invention, with the preferred cell line being from the human species.

Now that the entire sequence is known, the human IL-1δ, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with the IL-1ε or receptor sequences.

The IL-1δ protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, e.g., by extraction, precipitation, electrophoresis, various forms of chromatography, and the like. The interleukin of this invention can be obtained in varying degrees of purity depending upon its desired use. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the interleukin, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%–99% or more. Purity will usually be on a weight basis, but can also be on a molar basis. Different assays will be applied as appropriate.

VI. Antibodies

The term "antibody" or "antibody molecule" as used in this invention includes intact molecules as well as fragments thereof, such as Fab, F(ab')$_2$, and Fv which are capable of selectively binding the epitopic determinant. These antibody fragments retain some ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, e.g., Harlow and Lane (current edition) *Antibodies: A Laboratory Manual*, Cold Spring Harbor Laboratory, New York. Therefore, the phrase "antibody molecule" in its various forms as used herein contemplates both an intact antibody (immunoglobulin) molecule and an immunologically active portion of an antibody (immunoglobulin) molecule. Recombinant methods may be applied to make these fragments.

The term "monoclonal antibody" refers to a population of one species of antibody molecule of antigen-specificity. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen. In one embodiment, the first antibody molecule is affixed to a solid support.

As used in this invention, the term "epitope" means an antigenic determinant on an antigen to which the paratope of an antibody binds. Epitopic determinants usually consist of chemically active surface groupings such as amino acids or sugar side chains and usually have specific three dimensional structural characteristics, as well as specific charge characteristics.

The word "complex" as used herein refers to the product of a specific binding agent-target reaction. An exemplary complex is an immunoreaction product formed by an antibody-antigen reaction.

The term "antigen" refers to a polypeptide or protein that is able to specifically bind to (immunoreact with) an antibody and form an immunoreaction product (immunocomplex). The site on the antigen with which the antibody binds is referred to as an antigenic determinant or epitope, and the binding should be detectable, e.g., 2X, 5X or more above background.

A method of the invention for detection of antibodies that bind to novel epitopes in a sample is performed in vitro, e.g., in immunoassays in which the antibodies can be identified in liquid phase or bound to a solid phase carrier. In various embodiments, the method is performed with a capture antibody bound to a solid support, and/or the capture antibody is a monoclonal antibody molecule.

Examples of types of immunoassays which can be utilized to detect novel antibodies in a sample, include competitive and non-competitive immunoassays in either a direct or indirect format. Examples of such immunoassays are the radioimmunoassay (RIA) and the sandwich (immunometric) assay. Detection of the antibodies can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules are bound by adsorption from an aqueous medium, although other modes of affixation, such as covalent coupling or other well known means of affixation to the solid matrix can be used. Preferably, the first antibody molecule is bound to a support before forming an immunocomplex with antigen, however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody-containing solid support at protein binding sites on the surface that are not occupied by the antibody molecule.

A typical aqueous protein solution contains about 2–10 weight percent bovine serum albumin in PBS at a pH of about 7–8. The aqueous protein solution-solid support mixture is typically maintained for a time period of at least one hour at a temperature of about 4°–37° C. and the resulting solid phase is thereafter rinsed free of unbound protein.

The first preselected antibody can be bound to many different carriers and used to detect novel epitope binding antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation.

In addition, if desirable, an antibody for detection in these immunoassays can be detectably labeled in various ways. There are many different labels and methods of labeling known. Examples of the types of labels which can be used in the present invention include, e.g., enzymes, radioisotopes, fluorescent compounds, colloidal metals, chemiluminescent compounds, and bio-luminescent compounds. Many other suitable labels exist for binding to the monoclonal antibodies of the invention Antibodies which bind to IL-1δ or IL-1ε polypeptides of the invention can be prepared using an intact polypeptide or fragments containing peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the host animal, e.g., a mouse, a rat, or a rabbit.

If desired, polyclonal or monoclonal antibodies can be further purified, e.g., by binding to and elution from a matrix to which is bound the antigen to which the antibodies were raised. Many techniques are available for purification and/or concentration of polyclonal antibodies, as well as monoclonal antibodies. See, e.g., Coligan, et al. (current ed.) Unit 9, *Current Protocols in Immunology*, Wiley Interscience.

It is also possible to use the anti-idiotype antibody technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The preparation of polyclonal antibodies is well-known to those skilled in the art. See, e.g., Green, et al. "Production of Polyclonal Antisera" pages 1–5 in Manson (ed.) *Immunochemical Protocols* Humana Press; *Production of Polyclonal Antisera in Rabbits, Rats, Mice and Hamsters* section 2.4.1 in Coligan, et al. *Current Protocols in Immunology*.

The preparation of monoclonal antibodies likewise is conventional. See, e.g., Kohler and Milstein (1975) *Nature* 256:495–497; Coligan, et al. *Current Protocols* sections 2.5.1–2.6.7; and Harlow and Lane (1989). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al. *Current Protocols* sections 2.7.1–2.7.12 and 2.9.1–2.9.3; Barnes, et al. in *Methods in Molecular Biology*, Humana Press.

Therapeutic applications are conceivable for the antibodies of the present invention. For example, antibodies of the present invention may also be derived from subhuman primate antibody. General techniques for raising therapeutically useful antibodies in baboons may be found, e.g., in Goldenberg, et al. (1991) WO 91/11465; and Losman, et al. (1990) *Int. J. Cancer* 46:310–314.

Alternatively, a therapeutically useful anti-IL-1δ or anti-IL-1ε antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, e.g., by Orlandi, et al. (1989) *Proc. Nat'l Acad. Sci. USA* 86:3833–3837. Techniques for producing humanized monoclonal antibodies are described, e.g., by Jones, et al. (1986) *Nature* 321:522–525; Riechmann, et al. (1988) *Nature* 332:323–327; Verhoeyen, et al. (1988) *Science* 239:1534–1536; Carter, et al. (1992) *Proc. Nat'l Acad. Sci. USA* 89:4285–4289; Sandhu (1992) *Crit. Rev. Biotech.* 12:437–462; and Singer, et al. (1993) *J. Immunol.* 150:2844–2857.

Antibodies of the invention also may be derived from human antibody fragments isolated from a combinatorial immunoglobulin library. See, e.g., Barbas, et al. (1991) *Methods: A Companion to Methods in Enzymology*, vol. 2, page 119; and Winter, et al. (1994) *Ann. Rev. Immunol.* 12:433–465. Cloning and expression vectors that are useful for producing a human immunoglobulin phage library can be obtained, e.g., from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green, et al. (1994) *Nature Genet.* 7:13–21; Lonberg, et al. (1994) *Nature* 368:856–859; and Taylor, et al. (1994) *Int. Immunol.* 6:579–591.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a fragment denoted F(ab')$_2$. This fragment can be further cleaved using a thiol reducing agent, and optionally a blocking group for the sulfhydryl groups resulting from cleavage of disulfide linkages, to produce Fab' monovalent fragments. Alternatively, an enzymatic cleavage using papain produces two monovalent Fab fragments and an Fc fragment directly. These methods are described, e.g., by Goldenberg, U.S. Pat. Nos. 4,036,945 and No. 4,331,647, and references contained therein. These patents are hereby incorporated in their entireties by reference including all figures, drawings, and illustrations. See also Nisonhoff, et al. (1960) *Arch. Biochem. Biophys.* 89:230-et seq.; Porter (1959) *Biochem. J.* 73:119-et seq.; Edelman, et al. (1967) *Methods in Enzymology*, vol. 1, Academic Press; and Coligan, et al. *Current Protocols*, at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar, et al. (1972) *Proc. Nat'l Acad. Sci. USA* 69:2659-et seq. Alternatively, the variable chains can be linked by an intermolecular disulfide bond or cross-linked by chemicals such as glutaraldehyde. See, e.g., Sandhu (1992) *Crit. Rev. Biotech.* 12:437–462. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, e.g., by Whitlow, et al. (1991) *Methods: A Companion to Methods in Enzymology*, vol. 2, page 97; Bird, et al. (1988) *Science* 242:423–426; Ladner, et al., U.S.

Pat. No. 4,946,778; Pack, et al. (1993) *Bio/Technology* 11:1271–77; and Sandhu (1992) *Crit. Rev. Biotech.* 12:437–462.

Another form of an antibody fragment is a peptide coding for a single complementarity-determining region (CDR). CDR peptides ("minimal recognition units") can be obtained by constructing genes encoding the CDR of an antibody of interest. Such genes are prepared, e.g., by using the polymerase chain reaction to synthesize the variable region from RNA of antibody-producing cells. See, e.g., Larrick, et al. (1991) *Methods: A Companion to Methods in Enzymology*, vol. 2, page 106.

Antibodies can be raised to the various mammalian, e.g., IL-1δ and/or IL-1ε proteins and fragments thereof, both in naturally occurring native forms and in their recombinant forms, the difference being that antibodies to the active ligand are more likely to recognize epitopes which are only present in the native conformations. Denatured antigen detection can also be useful in, e.g., Western blot analysis. Anti-idiotypic antibodies are also contemplated, which would be useful as agonists or antagonists of a natural receptor or an antibody.

A number of immunogens may be used to produce antibodies specifically reactive with thymokine proteins. Recombinant protein is the preferred immunogen for the production of monoclonal or polyclonal antibodies. Naturally occurring protein may also be used either in pure or impure form. Synthetic peptides made using the human or mouse lymphotactin protein sequences described herein may also used as an immunogen for the production of antibodies to thymokines. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the antigen of interest. When appropriately high titers of antibody to the immunogen are obtained, blood is collected from the animal and antisera are prepared. Further fractionation of the antisera to enrich for antibodies reactive to the protein can be done if desired. See Harlow and Lane.

Monoclonal antibodies may be obtained by various techniques familiar to those skilled in the art. Briefly, spleen cells from an animal immunized with a desired antigen are immortalized, commonly by fusion with a myeloma cell. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better; including 1 µM, 300 nM, 100 nM, 30 nM, etc.

The antibodies, including antigen binding fragments, of this invention can have significant diagnostic or therapeutic value. They can be potent antagonists that bind to the interleukin and inhibit binding to the receptor or inhibit the ability of IL-1δ or IL-1ε to elicit a biological response. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the interleukin without inhibiting receptor binding. As neutralizing antibodies, they can be useful in competitive binding assays. They will also be useful in detecting or quantifying IL-1δ. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Primate IL-1δ and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed) Academic Press, New York; and particularly in Kohler and Milstein (1975) in *Nature* 256:495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," Science 246:1275–1281; and Ward, et al. (1989) Nature 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant or chimeric immunoglobulins may be produced, see Cabilly, U.S. Pat. No. 4,816,567; or made in transgenic mice, see Mendez, et al. (1997) Nature Genetics 15:146–156. These references are incorporated herein by reference.

The antibodies of this invention can also be used for affinity chromatography in isolating primate IL-1δ. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified protein will be released. Conversely, protein may be used to purify antibody.

Antibodies may also be used to screen expression libraries for particular expression products. Usually antibodies used in such a procedure will be labeled with a moiety allowing easy detection of presence of antigen by antibody binding.

Antibodies raised against an IL-1δ or IL-1ε will also be used to raise anti-idiotypic antibodies. These will be useful in detecting or diagnosing various immunological conditions related to expression of the protein or cells which express receptors for the protein. They also will be useful as agonists or antagonists of the interleukin, which may be competitive inhibitors or substitutes for naturally occurring ligands.

Binding Agent:IL-1δ/IL-1ε Protein Complex

An IL-1δ or IL-1ε protein that specifically binds to or that is specifically immunoreactive with an antibody, e.g., a polyclonal antibody generated against a defined immunogen, e.g., an immunogen consisting of an amino acid sequence of SEQ ID NO: 2, is typically determined in an immunoassay. Included within the present invention are those nucleic acid sequences described herein, including functional variants, that encode polypeptides that bind to polyclonal antibodies generated against the prototypical primate IL-1δ, but not the prior known rodent counterpart. The immunoassay typically uses a polyclonal antiserum which was raised, e.g., to a protein of SEQ ID NO: 2. This antiserum is selected to have low crossreactivity against other IL-1 family members, preferably from the same species, and to other rodent or similar evolutionarily distant IL-1δ, so that any such crossreactivity is removed by immunoabsorption prior to use in the immunoassay.

In order to produce antisera for use in an immunoassay, the protein of SEQ ID NO: 2 is isolated as described herein. For example, recombinant protein may be produced in a mammalian cell line. An appropriate host, e.g., an inbred strain of mice such as Balb/c, is immunized with the protein of SEQ ID NO: 2 using a standard adjuvant, such as Freund's adjuvant, and a standard mouse immunization protocol (see Harlow and Lane). Alternatively, a synthetic peptide derived from the sequences disclosed herein and conjugated to a carrier protein can be used an immunogen. Polyclonal sera are collected, perhaps immunodepleted, and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-1 family members, e.g., IL-1α, IL-1β, IL-1RA, IL-1γ, IL-1ε, and rodent IL-1δ using a competitive binding immunoassay such as the one described in Harlow and Lane, supra, at pages 570–573. Preferably at least two IL-1 family members are used in this determination in conjunction with rodent IL-1δ. These IL-1 family members can be produced as recombinant proteins and isolated using standard molecular biology and protein chemistry techniques as described herein.

Immunoassays in the competitive binding format can be used for the crossreactivity determinations. For example, the protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the IL-1 like protein of SEQ ID NO: 2). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 that is required, then the second protein is said to specifically bind to an antibody generated to the immunogen.

It is understood that these IL-1δ or IL-1ε proteins are members of a family of homologous proteins that comprise at least 5 so far identified genes. For a particular gene product, such as the IL-1δ or IL-1ε protein, the term refers not only to the amino acid sequences disclosed herein, but also to other proteins that are allelic, non-allelic or species variants. It is also understood that the term "IL-1δ" or "IL-1ε" includes nonnatural mutations introduced by deliberate mutation using conventional recombinant technology such as single site mutation, or by excising short sections of DNA encoding the respective proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring IL-1 related protein, e.g., the IL-1δ protein shown in SEQ ID NO: 2. The biological properties of the altered proteins can be determined by expressing the protein in an appropriate cell line and measuring the appropriate effect upon lymphocytes. Particular protein modifications considered minor would include conservative substitution of amino acids with similar chemical properties, as described above for the IL-1 family as a whole. By aligning a protein optimally with the protein of SEQ ID NO: 2 and by using the conventional immunoassays described herein to determine immunoidentity, one can determine the protein compositions of the invention.

VII. Kits and Quantitation

Both naturally occurring and recombinant forms of the IL-1 like molecules of this invention are particularly useful in kits and assay methods. For example, these methods would also be applied to screening for binding activity, e.g., receptors for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767–773, which is incorporated herein by reference. The latter describes means for testing binding by a plurality of defined polymers synthesized on a solid substrate. The development of suitable assays to screen for a receptor or agonist/antagonist homologous proteins can be greatly facilitated by the availability of large amounts of purified, soluble IL-1δ or IL-1ε in an active state such as is provided by this invention.

Purified IL-1δ can be coated directly onto plates for use in the aforementioned receptor screening techniques. However, non-neutralizing antibodies to these proteins can be used as capture antibodies to immobilize the respective interleukin on the solid phase, useful, e.g., in diagnostic uses.

This invention also contemplates use of IL-1δ, fragments thereof, peptides, and their fusion products in a variety of diagnostic kits and methods for detecting the presence of the protein or its receptor. Alternatively, or additionally, antibodies against the molecules may be incorporated into the kits and methods. Typically the kit will have a compartment containing either a defined IL-1δ peptide or gene segment or a reagent which recognizes one or the other. Typically, recognition reagents, in the case of peptide, would be a receptor or antibody, or in the case of a gene segment, would usually be a hybridization probe.

A preferred kit for determining the concentration of, e.g., IL-1δ, a sample would typically comprise a labeled compound, e.g., receptor or antibody, having known binding affinity for IL-1δ, a source of IL-1δ (naturally occurring or recombinant) as a positive control, and a means for separating the bound from free labeled compound, e.g., a solid phase for immobilizing the IL-1δ in the test sample. Compartments containing reagents, and instructions, will normally be provided.

Antibodies, including antigen binding fragments, specific for mammalian IL-1δ or a peptide fragment, or receptor fragments are useful in diagnostic applications to detect the presence of elevated levels of IL-1δ and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to IL-1δ or to a particular fragment thereof. These assays have also been extensively discussed in the literature. See, e.g., Harlow and Lane (1988) *Antibodies: A Laboratory Manual*, CSH., and Coligan (ed. 1991 and periodic supplements) *Current Protocols In Immunology* Greene/Wiley, New York.

Anti-idiotypic antibodies may have similar use to serve as agonists or antagonists of IL-1δ. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

Any of the aforementioned constituents of the diagnostic assays may be used without modification or may be modified in a variety of ways. For example, labeling may be achieved by covalently or non-covalently joining a moiety which directly or indirectly provides a detectable signal. In any of these assays, a test compound, IL-1δ, or antibodies thereto can be labeled either directly or indirectly. Possibilities for direct labeling include label groups: radiolabels such as $^{125}$I, enzymes (U.S. Pat. No. 3,645,090) such,as peroxidase and alkaline phosphatase, and fluorescent labels (U.S. Pat. No. 3,940,475) capable of monitoring the change in fluorescence intensity, wavelength shift, or fluorescence polarization. Both patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The IL-1δ can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a primate.IL-1δ. These sequences can be used as probes for detecting levels of the IL-1δ in patients suspected of having an immunological disorder, or to evaluate polymorphic variation. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

VIII. Therapeutic Utility

This invention provides reagents with significant therapeutic value. The IL-1δ or IL-1ε (naturally occurring or recombinant), fragments thereof, mutein agonists and antagonists, and antibodies, along with compounds identified as having binding affinity to the interleukin or its receptor or antibodies, should be useful in the treatment of conditions exhibiting abnormal expression of the interleukin. Such abnormality will typically be manifested by immunological disorders. Additionally, this invention should provide therapeutic value in various diseases or disorders associated with abnormal expression or abnormal triggering of response to the interleukin. The mouse IL-γ has been suggested to be involved in tumors, allergies, and infectious diseases, e.g., pulmonary tuberculosis, leprosy, fulminant hepatitis, and viral infections, such as HIV. The IL-1δ and/or IL-1ε or antagonist may have similar function, and the signaling has been shown to involve NFκB (nuclear factor κB).

In addition, the dendritic cell expression profile shows human IL-1γ primarily expressed in activated dendritic cells. Activated dendritic cells are also a major producer of IL-12, and it is thought that this dendritic cell produced IL-12 plays a major role in directing a Th1 type response. The combination of IL-1γ and IL-12 should be extremely potent in inducing IFN-γ, suggesting that IL-1δ or IL-1ε, or antagonists thereof, may have similar function. It is possible that the combination of pro-inflammatory cytokines under certain circumstances could lead to septic shock. An antagonist, mutein or antibody, could prove very useful in this situation.

See Rich (ed.) *Clinical Immunology: Principles and Practice*, Mosby.

Additionally, IL-1δ or IL-1ε being homologous members of the IL-1 family likely play a role in modulating of local and systemic inflammatory processes (see, Durum, et al. (1985) *Ann. Rev. Immunol.* 3:263–287), through the enhancement of blood flow, induction of chemoattractants, and the enhancement and adherence of adhesion molecules resulting in the accumulation of inflammatory cells such as macrophages and neutrophils at the site of inflammation. Additionally, it is likely that IL-1δ or IL-1ε induce fibroblast growth and may play a role in contributing to the pathogenesis of chronic inflammation, as in rheumatoid arthritis or periodontal disease.

IL-1δ or IL-1ε are also likely to play a role in systemic inflammatory reactions, such as fever, hypoglycemia, the acute phase response of the liver, reduced plasma iron and zinc, and increased plasma copper. A systemic reaction such as septic shock involves vasodilation, due to IL-1, most likely in combination with other cytokines, including, e.g., TNF, IFN-γ, and leukemia inhibitory factor (LIF). The newly described IL-1δ or IL-1ε are also likely to be similarly involved.

T helper cells mediate effector functions in infectious, allergic, or autoimmune diseases through production of cytokines. CD4+ T cells can be divided into Th1 and Th2 subsets on the basis of their cytokine profile upon antigen stimulation. Evidence has recently been obtained that Th1 and Th2 cells differ in responsiveness and receptor expression for IL-1 family molecules. See, e.g., Robinson, et al. (1997) *Immunity* 7:571–581. Whereas Th1 cells respond to IL-1γ, Th2 cells respond to IL-1α. This differential responsiveness between Th1 and Th2 cells to IL-1γ and IL-1α, respectively, may have profound implications for regulation of ongoing Th cell responses. The novel IL-1 molecules described here could play a similar role in either supporting a Th1 or Th2 response, depending on the presence or absence of their cognate IL-1 receptors on the cell surface of these immune cells; e.g., IL-1RD4 (ST2) is an orphan IL-1-like receptor exclusively expressed on the Th2 subset. See, e.g., Lohning, et al. (1998) *Proc. Nat'l Acad. Sci. USA* 95:6930–6935; and U.S. Ser. No. 09/040,714, which are incorporated herein by reference. The expression profile of the novel IL-1 proteins here described (in particular IL-1ε) indicates that IL-1ε could be the ligand for IL-1RD4 and, as such, could be important for Th2 effector function.

In the following, directed to IL-1δ, similar substitution of IL-1ε may be appropriate. Recombinant IL-1δ, mutein agonists or antagonists, or IL-1δ antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Receptor screening using IL-1δ or fragments thereof can be performed to identify molecules having binding affinity to the interleukin. Subsequent biological assays can then be utilized to determine if a receptor can provide competitive binding, which can block intrinsic stimulating activity. Receptor fragments can be used as a blocker or antagonist in that it blocks the activity of IL-1δ. Likewise, a compound having intrinsic stimulating activity can activate the receptor and is thus an agonist in that it simulates the activity of IL-1δ. This invention further contemplates the therapeutic use of antibodies to IL-1δ as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds 1990) *Goodman and Gilman's: The Pharmacological Bases of Therapeutics,* 8th Ed., Pergamon Press; and *Remington's Pharmaceutical Sciences,* (current ed.), Mack Publishing Co., Easton, Penn.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Because of the likely high affinity binding between an IL-1δ and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

IL-1δ fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds. 1993) *Pharmaceutical Dosage Forms: Parenteral Medications* Dekker, NY; Lieberman, et al. (eds. 1990) *Pharmaceutical Dosage Forms: Tablets* Dekker, NY; and Lieberman, et al. (eds. 1990) *Pharmaceutical Dosage Forms: Disperse Systems* Dekker, NY.

Another therapeutic approach included within the invention involves direct administration of reagents or compositions by any conventional administration techniques (e.g., but not restricted to local injection, inhalation, or administered systemically), to the subject with an inflammatory disorder. The reagent, formulation or composition may also be targeted to specific cells or receptors by any of the methods described herein. The actual dosage of reagent, formulation or composition that modulates an inflammatory disorder depends on many factors, including the size and health of an organism, however one of one of ordinary skill in the art can use the following teachings describing the methods and techniques for determining clinical dosages. See, e.g., Spilker (1984) *Guide to Clinical Studies and Developing Protocols,* Raven Press, New York, particularly pages 7–13, 54–60; Spilker (1991) *Guide to Clinical Trials,* Raven Press, New York, especially pages 93–101; Craig and Stitzel (eds. 1986) *Modern Pharmacology* 2d ed., Little, Brown, Boston, especially pages 127–33; Speight (ed. 1987) *Avery's Drug Treatment: Principles and Practice of Clinical Pharmacology and Therapeutics,* 3d ed., Williams and Wilkins, Baltimore, pages 50–56; and Tallarida, et al. (1988) *Principles in General Pharmacology,* Springer-Verlag, New York, pages 18–20; which describe how to determine the appropriate dosage; but, generally, in the range of about between 0.5 ng/ml and 500 μg/ml inclusive final concentration are administered per day to an adult in a pharmaceutically-acceptable carrier. The therapy of this invention may be combined with or used in association with other therapeutic agents, particularly agonists or antagonists of other IL-1 family members.

The IL-R6 receptor subunit forms the basis for a good candidate for an antagonist drug development (i.e., humanized anti-human IL-1R6 antibodies). IL-1R6 seems to be mainly expressed on resident epithelial cells, constituting the ports of entry to the body's internal milieu. IL-1R6 may form an integral part of the innate immune defense against exposure to external micro-organisms. IL-1R6's ligand, IL-1ε, activates NFκB, as do many pro-inflammatory mediators (e.g., LPS, IL-1s, and TNFs). NFκB is a transcription factor widely involved in the induction of expression of inflammatory mediators, such as numerous cytokines, chemokines, and their adhesion molecules. The increased expression of IL-1ε and IL-1R6 in chronically inflamed skin (e.g., psoriasis) points to the possible clinical relevance of this R6 signaling system. The fact that the other component of this system (IL-1δ) acts as a very potent antagonist might prove to have clinical use.

IX. Receptors

The description of the IL-1δ ligand herein provides means to identify a receptor, as described above. Such receptor should bind specifically to the IL-1δ with reasonably high affinity. Various constructs are made available which allow either labeling of the IL-1δ to detect its receptor. For example, directly labeling IL-1δ, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available IL-1δ sequences. See, e.g., Fields and Song (1989) *Nature* 340:245–246. Typically, a cytokine will bind to its receptor at a Kd of at least about 30 μM, preferably at least about 10 μM, and more preferably at least about 3 μM or better; including 1 μM, 300 nM, 100 nM, 30 nM, etc.

Generally, descriptions of how to make IL-1δ will be analogously applicable to embodiments directed to IL-1ε reagents and compositions.

Interleukin-1 (IL-1) is of utmost importance in the host responses to immunological challenges. IL-1 ligand as well as IL-1 receptor (R) isoforms affect and tightly control IL-1's net biological activity. This application, with earlier filings, reports identification of novel IL-1 ligands based on homology to IL-1 receptor antagonist (IL-1RA), which are termed IL-1δ and IL-1ε. RNA expression data showed that these IL-1s are highly expressed in embryonic tissue and tissues containing epithelial cells (e.g., skin, lung, and stomach). With respect to the skin, keratinocytes are the main producers of IL-1δ/ε. IL-1δ/ε proteins lack a classical leader sequence (as does secreted IL-1RA) or a clear pro-form (as do IL-1α/β/γ), but do get secreted in the supernatant of transiently transfected cells. Functionally, using nuclear factor κB (NFκB)-Luciferase reporter assays, it has been demonstrated that IL-1δ/ε proteins do not initiate a response through the classical pathway of other IL-1Rs, which confer responsiveness to either IL-1α/β (e.g., IL-1RI/IL-1R accessory protein) or IL-18/IL-1γ (e.g., IL-1R related protein 1/IL-1R accessory protein-like). However, when testing the orphan IL-1R-like molecules T1/ST2 and IL-1R related protein 2 (IL-1Rrp2), it was reproducibly found to activate NFκB upon stimulation with IL-1ε, but not IL-1δ. IL-1δ, showing the highest similarity to IL-1RA, on the other hand, specifically inhibited this IL-1Rrp2 response to IL-1ε. IL-1δ is, in fact, a highly potent antagonist for IL-1Rrp2, as the effective ratio between IL-1δ and IL-1ε is 3 orders of magnitude less than for IL-1R1 (e.g., IL-1RA:IL-1α).

IL-1δ and ε were identified computationally: Computational analyses led to the discovery of two novel IL-1 ligands: IL-1δ and IL-1ε. In short, the search strategies were based on homology and HMMer searches. A blast search with mouse IL-1RA revealed a public EST containing the entire open reading frame of mouse IL-1δ. Subsequently, the entire human IL-1δ sequence was found as part of a proprietary EST. Using mouse IL-1δ as a bait also led to the finding of a public EST containing a partial sequence of mouse IL-1ε, which was extended in the 5' direction to obtain the full length sequence. Another proprietary EST containing the full length human IL-1ε sequence was ultimately found by a HMMer search using a PFAM alignment of IL-1α, IL-1β, and IL-1RA.

IL-1δ and IL-1ε are highly expressed in embryonic tissue and in epithelial cells: Northern blot analyses show that the novel IL-1 ligands are expressed in embryonic tissue, and tissues containing epithelial cells (e.g., stomach and skin). Expression in lung tissue appeared unique to IL-1δ. It should also be noted that IL-1δ mRNA analysis shows the presence of multiple variants (as does IL-1RA). Hannum, et al. (1990) *Nature* 343:336–340; Eisenberg, et al. (1990) *Nature* 343:341–346; Haskill, et al. (1991) *Proc. Nat'l Acad. Sci. USA* 88:3681–3685; Muzio, et al. (1995) *J. Exp. Med.* 182:623–628; and Weissbach, et al. (1998) *Biochem. Biophys. Res. Commun.* 244:91–95. Additional studies, based on quantitative PCR, revealed that in skin, keratinocytes and langerhans cells, but not fibroblasts or skin-homing T cells, are the main producers of IL-1δ and IL-1ε.

IL-1δ and IL-1ε proteins are secreted: The novel IL-1 ligands are secreted as determined by their presence in the supernatant of transiently transfected 293-T cells. However, they do not have a classical leader sequence (as does secreted IL-1RA; Eisenberg, et al. (1990) *Nature* 343:341–346), nor do they have a clear pro-form (as do IL-1α/β/γ; March, et al. (1985) *Nature* 315:641–647; Okamura, et al. (1995) *Nature* 378:88–91; and Ushio, et al. (1996) *J. Immunol.* 156:4274–4279.

IL-1δ and IL-1ε do not activate NFκB through classical IL-1Rs: The ability of the novel IL-1s to initiate IL-1R-mediated signaling was studied via an NFκB-dependent reporter assay using ligand-stimulated Jurkat T cells transiently transfected with different pairs of IL-1Rs. The R1/R3 combination, being responsive to IL-1α and IL-1γ (Greenfeder, et al. (1995) *J. Biol. Chem.* 270:13757–13765; and Cullinan, et al. (1998) *J. Immunol.* 161:5614–5620, did not generate a response to IL-1δ or IL-1ε. Also, the R5/R7 combination, responsible for the response to IL-18/IL-1γ (Born, et al. (1998) *J. Biol. Chem.* 273:29445–29450), did not result in signaling upon addition of the novel IL-1 ligands. The next step was to test the orphan IL-1R-like molecules, IL-1R4 and IL-1R6 (classified as potential ligand-binding receptors, based on their homology to IL-1R1) in combination with various other IL-1R-like molecules, e.g., IL-1R3, IL-1R7, IL-1R9 and IL-1R10 (classified as potential signaling receptors, based on their homology to IL-1R3) for their responsiveness to IL-1δ and IL-1ε. These data consistently showed an IL-1R6-mediated activation of NFκB upon stimulation with IL-1ε, but not IL-1δ or the mock control.

IL-1δ specifically and very potently antagonizes the IL-1R6 response to IL-1ε: In line with the striking similarity between IL-1δ and IL-1RA, the possibility of IL-1δ being an antagonist of IL-1 responses was tested to distinguish from it being an IL-1 agonist. Using the same reporter assay, it was shown that IL-1RA, but not IL-1δ, is able to antagonize the IL-1R1-mediated activation of NFκB upon stimulation with IL-1α. Reciprocally, IL-1δ, but not IL-1RA, is able to antagonize the IL-1R6-mediated activation of NFκB upon stimulation with IL-1ε. One can conclude that IL-1RA shows a 50% inhibition of the IL-1R1 response at about a 1000-fold excess over IL-1α, whereas IL-1δ results in a similar inhibition of the IL-1R6 response at concentrations similar to or even less than IL-1ε.

The current application describes the discovery of two novel members of the IL-1 family. This is in extension to recent reports on new IL-1 family members (Mulero, et al. (1999) *Biochem. Biophys. Res. Commun.* 263:702–706; Smith, et al. (2000) *J. Biol. Chem.* 275:1169–1175; and U.S. Ser. No. 09/130,972. The present report is unique in several aspects. First, it is shown that these novel IL-1s have a restricted expression pattern, with a high expression in epithelial cells. Second, it has been possible to express and purify adenovirus-derived human IL-1δ and IL-1ε proteins which show function, e.g., they affect IL-1 signaling mediated through the orphan IL-1R-like molecule, IL-1R6 (e.g., IL-1Rrp2). Third, the novel IL-1 ligands together with IL-1R6, constitute a novel IL-1R system with IL-1ε acting as an agonist and IL-1δ as an antagonist in analogy to the IL-1R1 system with IL-1α and IL-1β acting as agonists and IL-1RA as an antagonist.

A structurally-aided alignment of the novel IL-1s and the classical IL-1s indicates the conservation of core 12 β-strands, making up a β-trefoil structure. At the sequence level, IL-1δ and IL-1RA show a high degree of similarity, which is also evident from the evolutionary tree analysis. With respect to IL-1ε, it is interesting to note that several public mouse ESTs exist, mostly derived from tongue epithelium, with only slight variations relative to the presented IL-1ε sequence. In addition, FIL-1ε (Smith, et al. (2000) *J. Biol. Chem.* 275:1169–1175) also shows a very high similarity to the human IL-1ε sequence provided (e.g., 51%). How these IL-1ε variants are generated and their biological significance remain unclear. The IL-1δ and IL-1ε genes cluster together and are localized to the same region of chromosome 2 q as the IL-1α, IL-1β, and IL-1RA genes (see also Mulero, et al. (1999) *Biochem. Biophys. Res. Commun.* 263:702–706; and Smith, et al. (2000) *J. Biol. Chem.* 275:1169–1175), stressing the notion that these IL-1 family members are all derived from a common ancestor.

IL-1δ and IL-1ε have a strong expression in embryonic development, and in tissues such as stomach, lung and skin. Lung tissue only showed IL-1δ mRNA expression, although at PCR level, expression of both isoforms can be detected in lung-derived cDNAs. The predominant messages for IL-1δ are 1.2 and 2.6 kb for stomach and skin tissues and 2.0 kb for lung tissue. It is of interest to note that IL-1δ mRNA in lung tissue appears to lack an exon relative to other tissues. Smith, et al. (2000) *J. Biol. Chem.* 275:1169–1175. Therefore, the different messages might in fact reflect different (tissue-specific) splice variants, as seen for IL-1RA (Hannum, et al. (1990) *Nature* 343:336–340; Eisenberg, et al. (1990) *Nature* 343:341–346; Haskill, et al. (1991) *Proc. Nat'l Acad. Sci. USA* 88:3681–3685; Muzio, et al. (1995) *J. Exp. Med.* 182:623–628; and Weissbach, et al. (1998) *Biochem. Biophys. Res. Commun.* 244:91–95. Tissue distribution and presence of differently sized messages of IL-1RA was strikingly similar to that of IL-1δ. Expression of IL-1δ variants might be, in line with IL-1RA, under the control of different promotors (Butcher, et al. (1994) *J. Immunol.* 153:701–711). A more detailed look at human skin, using quantitative PCR analysis of a panel of first strand cDNAs derived from various skin-specific cell types, pointed to keratinocytes, and not fibroblasts or skin-homing T cells, as the major source of these IL-1s. Preliminary in situ hybridisation data using mouse tissue sections confirmed that cells of epithelial origin, such as the parietal and chief cells in stomach, and basal keratinocytes in skin are the predominant cellular sources of these IL-1s. Because of their presence in epithelial barriers of the body (e.g., skin, digestive and respiratory tracts), one could speculate that IL-1δ and IL-1ε fulfill similar roles as their known family members (e.g., IL-1α and IL-1β) to promote a response to injury or infection. Dinarello (1994) *Eur. Cytokine Netw.* 5:517–531; and Kupper (1989) [published erratum appears in (1989) *Arch. Dermatol.* 125(12):1643] *Arch.Dermatol.* 125:1406–1412. Activities crucial to such a response include control of the proliferative status of epithelial cells, tissue remodelling (via matrix metalloproteinases) and production of pro-inflammatory molecules (e.g., cytokines, chemokines, their receptors and adhesion molecules). In non-cornified stomach epithelium, having a high expression of IL-1δ and IL-1ε relative to IL-1α and IL-1β, the novel IL-1s might display more unique functions, e.g., promoting cross-talk between stomach epithelial cells and the underlying (sub)mucosa-associated immune cells.

IL-1s are thought to function intracellularly under certain conditions, as suggested by the intracellular localization of pro-IL-1α (which is biologically active; see, Mosley, et al. (1987) *J. Biol. Chem.* 262:2941–2944) and intracellular IL-1RA isoforms in several epithelia (Dinarello (1994) *Eur. Cytokine Netw.* 5:517–531; and Arend (1993) *Adv.Immunol.* 54:167–227). The observation that the novel IL-1s lack a signal peptide as well as a clear pro-form, leads one to suppose that these new IL-1 proteins may be retained intracellularly. However, monitoring the presence of C-terminally tagged versions of IL-1δ and IL-1ε in the supernatants and lysates of transfected cells showed that these molecules do get secreted efficiently. The presence of alternate splice forms of IL-1δ leaves open the possibility that other forms of IL-1δ do exist. Such would agree with Thomassen, et al. (1999) *Cytokine* 11:389–399, who showed that the novel IL-1R-like molecule SIGIRR (e.g., IL-1R8) expresses as a glycosylated transmembrane protein without having an obvious signal peptide, and concluded that this probably reflects limitations in our understanding of extracellular protein transport.

To study whether the novel IL-1s function like the classical IL-1s, the genes were expressed and purified as adenovirus-derived human IL-1δ and IL-1ε, and tested for their capacity to initiate IL-1 signaling, with an NFκB reporter assay as a read-out. The observation that the classical IL-1R pairs IL-1R1/3 and IL-1R5/7 do not respond to these new protein preparations might be explained by the fact that receptor-ligand combinations within the IL-1 system are very specific. Therefore, 1L-1R4 and IL-1R6 were tested in combination with various other IL-1R-like molecules. These studies consistently showed the usage of IL-1R6 by IL-1ε, but not IL-1δ, to activate NFκB in Jurkat cells. Even IL-1R6 single transfection showed this response. The IL-1 system, as understood today, typically requires two receptors, one ligand-binding receptor and one signaling receptor, to get an IL-1 response. Since IL-1R6 is very homologous to IL-1R1 (Lovenberg et al. (1996) *J. Neuroimmunol.* 70:113–122), a ligand-binding type of receptor, it as supposed that Jurkat cells endog nously express a second signaling type of receptor that can pair with IL-1R6 in the presence of IL-1ε. By PCT analysis, the following IL-1R-like molecules are expressed by untransfected Jurkat cells IL-1R3, IL-1R4, IL-1R8 (e.g., SIGIRR), and IL-IR9. Co-transfection of IL-1R6 with IL-1 R3, IL-1 R9, or IL-1R10 does not potentiate the response IL-1ε relative to IL-1R6 single transfectants. In addition, studies by others using IL-IR1 chimaeras and an IL-1α-mediated activation of NFκB as a read-out do not seem to favor the combination of IL-1R6 and IL-1R8 to mediate an IL-1 response. Thomassen, et el. (1999) *Cytokine* 11:389–399. The search for the additional IL-1ε receptor(s) is currently ongoing.

IL-1δ is most closely related to IL-1RA, and, like IL-1RA lacks the loop between the fourth and fifth β-strands which is typical for IL-1 agonists: IL-1α, IL-1β, IL-1γ, and IL-1ε. Insertion of the loop amino acids QG . . . SN of IL-1β confers, in fact, agonist activity to IL-1RA. Greenfeder, et al. (1995) *J. Biol. Chem.* 270:22460–22466. In extension of the striking similarity between IL-1δ and IL-1RA, it was hypothesized that IL-1δ might act as an antagonist. Experimentally, IL-1δ turned out to be a very specific and potent antagonist. It still antagonizes the IL-1R6-mediated response to IL-1ε at a ratio of IL-1δ: IL-1ε being less than 1. The potency of IL-1RA to antagonize the R1-response to IL-1α/β is about 3 orders of magnitude less. The observation by others (Smith, et al. (2000) *J. Biol. Chem.* 275:1169–1175) that their IL-1δ and IL-1ε do not bind to IL-1R6 is in our opinion not contradictory to our findings. Binding studies using partially purified IL-1δ and IL-1ε proteins from conditioned medium of transfected cells and an Fc fusion of IL-1R6 might not be sensitive enough to show binding to these new IL-1s. Moreover, the second receptor might actually be needed for affinity conversion and for binding to become detectable.

Expression of human IL-1R6 is limited when compared to human IL-1R1 or R3, which are expressed ubiquitously, and is restricted to lung epithelium and brain vasculature. Lovenberg, et al. (1996) *J. Neuroimmunol.* 70:113–122. Expression of IL-1R6 was found in monocytes and in skin-derived keratinocytes and fibroblasts, indicating that these cell types might be IL-1ε responding cells. Preliminary data indicate that the expression of IL-1δ, IL-1ε, and IL-1R6 are increased in lesional psoriasis skin samples relative to normal control skin samples. These data are being followed up, but indicate a clinical relevance of these novel IL-1 ligands.

Taken together, IL-1δ, IL-$_1$ε, and IL-1R6 probably constitute a system on their own, in analogy to IL-1α/β/ra and IL-1R1. This IL-1R6 system, present in epithelial barriers of the body, is, as a result of the co-expression of IL-1δ and IL-1ε, likely to have a default off-state. Perturbation of homeostasis, however, can shift this balance to a protective IL-1ε-mediated inflammatory or proliferative response.

The broad scope of this invention is best understood with reference to the following examples, which are not intended to limit the inventions to the specific embodiments.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms an expression of excluding any equivalents of the features shown and described or portions thereof, but it is recognized that various modifications are possible with the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Meth. Enzymol.*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression&Protein Purification System* QIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-4 and IL-10 may be applied to IL-1δ and/or IL-1ε, as described, e.g., in U.S. Pat. No. 5,017,691 (IL-4), U.S. Ser. No. 07/453,951 (IL-10), U.S. Ser. No. 08/110,683 (IL-10 receptor), and U.S. Ser. No. 09/130,972 (rodnet IL-1δ and rodent and primate IL-1ε) each of which is incorporated herein by reference for all purposes. Biological Reagents and Cell culture: Recombinant human IL-1α, IL-1β, IL-4, and IFNγ were provided by R&D Systems. Recombinant human IL-18/IL-1γ, IL-1RA and IL-10 were produced at DNAX. The Q293 and 293-T cell lines were maintained in DMEM supplemented with 5% fetal bovine serum, 0.3 mg/ml L-glutamine, 100 U/ml penicillin G, and 100 µg/ml streptomycin (Life Technologies, Inc.). Human primary epidermal keratinocytes and dermal fibroblasts (Clonetics) were cultured in specialized growth media according to the supplier's recommendations. The Jurkat E6.1 cell line was maintained in RPMI 1640 medium supplemented with 10% fetal bovine serum, glutamine, and antibiotics.

II. Amplification of IL-1δ or IL-1ε Fragment by PCR

Cloning of human and mouse IL-1δ and IL-1ε: See U.S. Ser. No. 09/130,972, which is incorporated herein by reference. Briefly, searching public expressed sequence tag (EST) database with the common portion of murine IL-1RA revealed EST mb49b11.r1 (Genbank accession # W08205), which contained the full-length sequence of a novel rodent IL-1-like molecule, designated IL-1δ. Using the mouse sequence as a query, a human EST derived from RNA from bronchial smooth muscle cells was found in a proprietary database containing the full-length open-reading frame of a human homologue of mouse IL-1δ. The same query sequence revealed an additional EST mi08c10.r1 (Genbank accession #AA030324), which contained partial sequence of a second novel IL-1-like molecule, designated IL-1ε. The full-length sequence of murine IL-1ε was obtained by extending the 5' sequence by RACE-PCR on murine 17 d old embryo Marathon-Ready library cDNA (Clontech). Finally, a HMMer (http://hmmer.wustl.edu/) search using a PFAM alignment of IL-1α, IL-1β and IL-1RA (http://pfam.wustl.edu/) revealed an EST derived from RNA from epithelial cells in a second proprietary database, which contained the full-length open-reading frame of the human IL-1ε.

The novel IL-1 sequences were aligned to the published IL-1 sequences using CLUSTALW (Thompson, et al. (1994) *Nucleic Acids Res.* 22:4673–4680), guided by tertiary structures and predicted secondary structures (with a consensus derived from several algorithms at http://circinus.ebi.ac.uk:8081/submit.html), and fine-tuning by eye. Conserved alignment patterns were drawn by Consensus (http://www.bork.emblheidelberg.de/Alignment/consensus.html). Evolutionary tree analysis was performed using a neighbor-joining algorithm and viewed using TreeView 1.5.

The IL-1 ligands appear to contain twelve conserved β-strands, particularly with the human IL-1β and IL-1RA. See, e.g., Vigers, et al. (1997) *Nature* 386:190–194; and Schreuder, et al. (1997) *Nature* 386:194–200. These are based, in part, on predicted secondary structures. Particular residues of human IL-1β which interact with IL-1R1 (sites A and B) have been described, and reflect on residues of other family members which structurally are predicted to interact with receptor subunits. See Ju, et al. (1991) *Proc. Nat'l Acad. Sci. USA* 88:2658–2662.

There are various methods of isolating the DNA sequences encoding IL-1δ and IL-1ε proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding thymokine proteins, or probes can be designed for use in amplification techniques such as PCR, for the isolation of DNA encoding IL-1δ and IL-1ε proteins.

Various methods of amplifying target sequences, such as the polymerase chain reaction, can also be used to prepare DNA encoding IL-1δ and IL-1ε proteins. Polymerase chain reaction (PCR) technology is used to amplify such nucleic acid sequences directly from mRNA, from cDNA, and from genomic libraries or cDNA libraries. The isolated sequences encoding IL-1δ or IL-1ε proteins may also be used as templates for PCR amplification.

In PCR techniques, oligonucleotide primers complementary to two 5' regions in the DNA region to be amplified are synthesized. The polymerase chain reaction is then carried out using the two primers. See Innis et al. (current eds.) *PCR Protocols: A Guide to Methods and Applications* Academic Press, San Diego, Calif. Primers can be selected to amplify the entire regions encoding a full-length IL-1δ or IL-1ε proteins or to amplify smaller DNA segments as desired. Once such regions are PCR-amplified, they can be sequenced and oligonucleotide probes can be prepared from sequence obtained using standard techniques. These probes can then be used to isolate DNA's encoding tIL-1δ or IL-1ε proteins.

Oligonucleotides for use as probes are chemically synthesized according to the solid phase phosphoramidite triester method first described by Beaucage and Carruthers (1983) *Tetrahedron Lett.* 22(20): 1859–1862, or using an automated synthesizer, as described in Needham-VanDevanter et al. (1984) *Nucleic Acids Res.* 12: 6159–6168. Purification of oligonucleotides is performed e.g., by native acrylamide gel electrophoresis or by anion-exchange HPLC as described in Pearson and Regnier (1983) *J. Chrom.* 255: 137–149. The sequence of the synthetic oligonucleotide can be verified using the chemical degradation method of Maxam and Gilbert in Grossman and Moldave (eds. 1980) *Methods in Enzymology* 65:499–560 Academic Press, New York.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library Complementary sequences will also be used as probes or primers. Based upon identification of the likely amino terminus, other peptides should be particularly useful, e.g., coupled with anchored vector or poly-A complementary PCR techniques or with complementary DNA of other peptides.

To identify a homologous IL-1δ or IL-1ε proteins, degenerate oligonucleotides are designed which corresponded to conserved regions among known IL-1 family members. The primers are used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known IL-1 family members.

Subsequently, PCR products are gel-purified, digested with appropriate restriction enzymes, gel-purified again, and subcloned in the Bluescript vector (Stratagene, San Diego, Calif.). Bacterial colonies carrying individual subclones are picked into 96 well microtiter plates, and multiple replicas are prepared by plating the cells onto nitrocellulose. The replicate filters are hybridized to probes representing known members of the IL-1 family, and DNA is prepared from non-hybridizing colonies for sequence analysis.

Two appropriate forward and reverse primers are selected using the sequences supplied herein (see SEQ ID Nos:1 and 3) and common knowledge. See, e.g., Innis, et al. (current eds.) *PCR Protocols: A Guide to Methods and Applications* Academic Press, San Diego, Calif.; and Dieffenbach and Dveksler (current eds.) *PCR Primer: A Laboratory Manual* Cold Spring Harbor Press, CSH, NY. RT-PCR is used on an appropriate mRNA sample selected for the presence of message to produce a cDNA, e.g., a monocyte or macrophage cell sample. The original isolate of IL-1δ was from a whole mouse cDNA library, and for the IL-1ε from a mouse placenta.

Full length clones may be isolated by hybridization of cDNA libraries from appropriate tissues pre-selected by PCR signal.

As is commonly known, PCR primers are typically designed to contain at least 15 nucleotides, e.g., 15–30 nucleotides. The design of IL-1δ or IL-1ε specific primers containing 21 nucleotides, e.g., that code for IL-1δ or IL-1ε polypeptides containing at least 4 amino acids from the IL-1δ or IL-1ε domains are described as follows. Other PCR primers designed to amplify other IL-1δ or IL-1ε polypeptide fragments will be designed in a similar fashion, e.g., mutagenesis primers. Preferably, most or all of the nucleotides in such a primer encode conserved amino acids, e.g., amino acid residues of SEQ ID NO: 2 or 4, including IL-1δ or IL-1ε-specific amino acids as described herein. For example, primers containing at least 40% IL-1δ or IL-1ε-conserved amino acids can be used. Such a primer, containing 21 nucleotides, can include sequences encoding at least 3/7, 4/7, 5/7, 6/7 or 7/7 IL-1δ or IL-L1ε-conserved amino acids. Once IL-1δ or IL-1ε amino acids are selected as templates against which primer sequences are to be designed, the primers can be synthesized using, e.g., standard chemical methods. Due to the degeneracy of the genetic code and the bias of preferred species variants, such primers should be designed to include appropriate degenerate sequences, as can be readily determined using common knowledge.

As is described above, IL-1ε or IL-1δ primers, e.g., primers based on IL-1ε or IL-1δ specific peptides shown above, or portions thereof, can be used in PCR reactions to generate IL-1ε or IL-1δ, probes which can be used in standard screening methods to identify nucleic acids encoding IL-1ε or IL-1δ family members (see, e.g., Ausubel, et al., supra).

III. Tissue Distribution of IL-1δ or IL-1ε

Message for the gene encoding IL-1δ has been detected in a mouse cDNA library. Message for IL-L1ε has been detected in placenta tissue.

Southern Analysis: DNA (5 µg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation could include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO− T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D109); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

Using the information described herein for cloning species variants, expression of human IL-1ε or IL-1δ can be determined as above using a human homologue as for a detectable probe.

Tissue distribution of transcripts derived from IL-1δ and IL-1ε were determined in experiments using an RNAse protection assay. Total RNA was prepared from adult brain, spleen, lung, liver and kidney by homogenization in guanidium thiocyantae and extraction with phenol, followed by centrifugation through 5.7 M cesium chloride (Sambrook, et al. (1987 and periodic updates) *Molecular Cloning: A laboratory Manual* Cold Spring Harbor Laboratory Press, Cold Spring Harbor, N.Y.). Ten micrograms of total RNA from each tissue, or ten micrograms of yeast tRNA, was used for RNAse protection assay. Riboprobes were synthesized using either T7 or T3 RNA polymerase on linerized templates that were cloned into pBluescript. Each mouse IL-1δ and IL-1ε probe contained 150–200 nucleotides from the antisense strand, linked to 25–50 nucleotides of vector sequence. Reagents were obtained from Ambion (Austin, Tex.) following standard manufacturer's protocols.

Tissue distribution of transcripts derived from IL-1δ and IL-1ε were compared with IL-1γ. The results demonstrate that IL-1ε expression is detectable in both embryonic, postnatal, and adult mice. An IL-1ε transcript (about 1.35 kD) is detectable at gestational day 7 and on postnatal day 1, adult IL-1δ transcripts (about 1.35 kD) were detectable in both the lung and kidney while not detected in brain, spleen and liver. For IL-1δ, an approximate 1.35 kD transcript was strongly detectable at gestational day 15 with a larger sized transcript (approximately 3.5 kD) less strongly detected. Similar results were observed at postnatal day 1. In adult tissue, a single sized IL-1δ transcript (approximately 1.8 kD) was detected in lung, liver, and kidney.

Northern blot: Mouse Northern blots containing approximately 2 μg poly(A)+ RNA per lane, derived from either total embryo at different days post gestation (Clontech) or from different tissues (Origene Technologies, Inc.), were hybridized to the mouse IL-1δ and IL-1ε cDNA probes containing the complete open reading frames. Probes were labeled with $^{32}$P using the Redivue labeling kit (Amersham). Prehybridization, hybridization, stringency washes and stripping were carried out according to the manufacturer's protocols. Membranes were exposed to a phosphorimager.

Quantitation of mRNA expression: A panel of various human skin-derived cell lines or cells, such as fibroblast and keratinocyte cell lines, and freshly isolated T cells and Langerhans cells, were used for Taqman-PCR analyses. Fibroblast and keratinocyte cells were left untreated or were treated with IL-10 (at 300 ng/ml final), IL-4 (50 ng/ml), or IFNγ (20 ng/ml) for either 6 or 18 h before RNA was isolated. RNA was isolated by the guanidium/phenol method. Chomczynski and Sacchi (1987) *Anal. Biochem.* 162:156–159. T cell and Langerhans RNA samples were kindly donated by Dr. T. S. Kupper (Harvard Skin Disease Research Center, Boston, Mass.). The reverse transcriptase reactions were performed with SuperScript™II (Gibco BRL) according to the supplier's instructions, except that random hexamers (Promega Corp.), at a final concentration of 1 mM, were added to the reaction. cDNAs (50 ng per reaction) were analyzed for the expression of IL-1δ and IL-1ε genes by the Fluorogenic 5'-nuclease PCR assay (Holland, et al. (1991) *Proc. Nat'l Acad. Sci. USA* 88:7276–7280), using a Perkin-Elmer ABI Prism 7700 Sequence Detection System. Reactions were incubated for 2 min at 50°, denatured for 10 min at 95° C. and subjected to 40 two-step amplification cycles with annealing/extension at 60° C. for 1 min followed by denaturation at 95° C. for 15 sec. The amplicons for human IL-1δ and human IL-1ε were analyzed with FAM-labeled probes. 18S RNA quantities were measured with a VIC-labeled probe and served as internal controls to normalize for the total amount of cDNA. Values are expressed as fg/50 ng total cDNA.

IV. Cloning of Species Counterparts of IL-1δ and IL-1ε

Various strategies are used to obtain species counterparts of mouse IL-1δ and IL-1ε. One method is by cross hybridization using closely related species DNA probes. The degree of identity between mouse and human IL-1 counterparts typically is as high as 70%. It may be useful to go into evolutionarily similar species as intermediate steps. Another method is by using specific PCR primers based on the identification of blocks of similarity between human and mouse IL-1 counterparts, e.g., areas of highly conserved polypeptide sequence.

In addition, the IL-1α, IL-1β, and IL-1RA genes cluster on the same human chromosome. The fourth known member of the IL-1 family, IL-1γ, which is most closely related to IL-1β, has been mapped to a different human chromosome. Duplication of the intact IL-1α, IL-1β, IL-1RA gene cluster, a potential genetic event explaining a proliferation of additional family members, would suggest the existence of two as yet unidentified IL-1 genes at the location of the IL-1γ locus. IL-1δ and IL-1ε are potential candidates, and sequencing of the human IL-1γ locus may well lead to identification of the novel IL-1 genes.

V. Production of Mammalian IL-1δ Protein

An appropriate, e.g., GST, fusion construct is engineered for expression, e.g., in E. coli. For example, a mouse IGIF pGex plasmid is constructed and transformed into E. coli. Freshly transformed cells are grown in LB medium containing 50 μg/ml ampicillin and induced with IPTG (Sigma, St. Louis, Mo.). After overnight induction, the bacteria are harvested and the pellets containing IL-1δ are isolated. The pellets are homogenized in TE buffer (50 nM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the IL-1δ is filtered and passed over a glutathione-SEPHAROSE column equilibrated in 50 mM Tris-base pH 8.0. The fractions containing the IL-1δ-GST fusion protein are pooled and cleaved with thrombin (Enzyme Research Laboratories, Inc., South Bend, Ind.). The cleaved pool is then passed over a Q-SEPHAROSE column equilibrated in 50 mM Tris-base. Fractions containing IL-1δ are pooled and diluted in cold distilled $H_2O$, to lower the conductivity, and passed back over a fresh Q-SEPHAROSE column. Fractions containing IL-1δ are pooled, aliquoted, and stored in the −70° C. freezer.

Comparison of the CD spectrum with mouse IL-1β may suggest that the protein is correctly folded. See Hazuda, et al. (1969) J. Biol. Chem. 264:1689–1693.

Similar techniques will be applicable to a full length IL-1ε.

Protein expression and purification of human IL-1δ and IL-1ε: Adenoviral vectors containing full-length human IL-1δ and IL-1ε were constructed by PCR and used to transfect Q293 packaging cells. Produced viruses were subsequently purified, with all procedures according to manufacturer's protocols (Invitrogen). IL-1 proteins were prepared from $5 \times 10^8$ infected Q293 cells (adenoviruses at 10 MOI) which were subsequently incubated for 5 days in a cell factory in a total volume of 1l of serum-free CMF-1 medium (Gibco BRL). Culture medium was dialyzed (Spectra/Por membrane tubing, MW cut off: 6–8 kD) against 50 mM Tris-HCl, pH 8.0, 1 mM EDTA, and subsequently passed over Hitrap Q sepharose and Heparin columns. The flow-through, containing the IL-1 proteins, was sterile-filtered and concentrated approximately 70 times using an Amicon 8400 ultrafiltration cell with a 10 kD MW cut off membrane. The samples were dialyzed against PBS, and the protein content quantified by PAGE and Coomassie Blue staining using lysozyme as a standard. Protein identities were confirmed by N-terminal sequencing. Identically treated Q293 cells infected with adenovirus encoding green fluorescent protein provided a mock control. Endotoxin levels were determined using the Limulus Amebocyte Lysate assay (BioWhittaker) and were less then 4 EU/ml. Protein samples were stored at 40° C.

Expression vectors: For mammmalian expression, vectors encoding full-length human R1, mouse R3, mouse R4 and human R5 were constructed by inserting PCR-generated cDNA fragments into pME18S. Kitamura, et al. (1991) Proc. Nat'l Acad. Sci. USA 88:5082–5086. Human IL-1R6 was a generous gift of Dr. R. A. Maki (Neurocrine Biosciences, Inc., San Diego, Calif.), and both human IL-1R6 and IL-1R7 cDNA were subcloned directly into pME18S. For secretion studies, full-length mouse IL-1δ and IL-1ε were fused to a C-terminal E-tag and put into pCDM8 (Stratagene Cloning Systems) via PCR. pCDM8 constructs containing mouse IL-1δ or IL-1ε fused to an N-terminal exogenous SLAM leader (Castro, et al. (1999) J. Immunol. 163:5860–5870), and the extracellular part of mouse IL-1R7 fused to a C-terminal IgG module served a positive controls. The reporter gene plasmid pNFκB-Luc (Stratagene) contains five NFκB sites and a basic promoter element to drive luciferase expression, and pRSV-βGal results in constitutive expression of β-galactosidase.

VI. Secretion Studies

293-T cells were transfected with mouse IL-1δ and IL-1ε pCDM8:E-tag expression constructs with and without an N-terminal exogenous SLAM leader sequence using $Ca_3(PO_4)_2$ (5 Prime) according to the supplier's protocol. Cells were cultured in CMF-1 medium. Seventy-two hours post transfection, supernatants and lysates were collected, and screened for E-tagged proteins by Western blotting according to standard procedures.

VII. Signal Pathway Analysis

Reporter assay: For reporter gene assays, Jurkat E6.1 cells ($4 \times 10^6$) were transiently transfected by electroporation (300 V, 960 microfarad) with 2 μg pNFκB-Luc reporter gene plasmid, 0.5 μg of pRSV-βGal and 4 μg of each receptor-encoding DNA. Twenty hours post-transfection, cells were stimulated with 20 ng/ml of human IL-1α, IL-1β, IL-18/IL-1γ, or IL-1RA, or 50 ng/ml human IL-1δ or IL-1ε for 6 h. Cells were lysed using Reporter Lysis Buffer (Promega) and luciferase and β-galactosidase activities were assessed using Luciferase Assay Reagent (Promega) and Galacto-Light Kit (Tropix), respectively. Luciferase activities (in RLU) were normalized on the basis of β-galactosidase activities. For inhibition studies of IL-1R1-mediated activation of NFκB, IL-1α was used at 50 pg/ml and IL-1RA and IL-1δ were used at concentrations ranging from 10 μg/ml to 10 pg/ml. Inhibition of the IL-1R6-mediated response was done with IL-1ε used at 50 ng/ml and IL-1δ and IL-1RA at concentrations ranging from 10 μg/ml to 64 pg/ml.

The ability of the novel IL-1s to initiate IL-1R-mediated signaling was studied via an NFκB-dependent reporter assay using ligand-stimulated Jurkat T cells transiently transfected with different pairs of IL-1Rs. The R1/R3 combination, conferring responsiveness to IL-1α and IL-1β (Cullinan et al. (1998) J. Immunol. 161:d5614–5620; and Greenfeder et al. (1995a) J. Biol. Chem. 270:13757–13765), did not generate a response to IL-1δ or IL-1ε. Also, the R5/R7 combination, required to mediate a response to IL-18 (Born et al. (1998) J. Biol. Chem. 273:29445–29450), did not result in signaling upon addition of the novel IL-1 ligands. The next step was to test the orphan IL-1R-like molecules IL-1R4 and IL-1R6, classified as potential ligand-binding receptors based on their homology to IL-1R1 (Sana, et al. (2000) *Genomics* 69:252–262), in combination with various other IL-1R-like molecules, i.e., IL-1R3, IL-1R7, IL-1R9 and IL-1R10 (classified as potential signaling receptors based on their homology to IL-1R3 (Sana, et al. supra.) for their potential to confer responsiveness to IL-1δ and IL-1ε. Data consistently showed an IL-1R6-mediated activation of NFκB upon stimulation with IL-1ε, but not IL-1δ or the mock control.

In line with the striking similarity between IL-1δ and IL-1ra, the possibility of IL-1δ being an antagonist of IL-1 responses rather than being an IL-1 agonist was tested. Using the same reporter assay, it was shown that IL-1ra but not IL-1δ is able to antagonize the IL-1R1-mediated activation of NFκB upon stimulation with IL-1α. Vice versa, IL-1δ but not IL-1ra, is able to antagonize the IL-1R6-mediated activation of NFκB upon stimulation with IL-1ε. Importantly, IL-1ra shows a 50% inhibition of the IL-1R1-mediated response to IL-1α at about a 1000-fold excess over IL-1α, whereas IL-1δ results in a similar inhibition of the IL-1R6 response at concentrations similar to or even less than IL-1ε.

In lesional psoriasis skin, characterized by chronic cutaneous inflammation, the expression of the IL-1 ligands IL-1δ and IL-1ε and their corresponding receptor IL-1R6 are all significantly increased relative to skin from a healthy individual. The increase is most prominent for IL-1ε, in line with in vitro-cultured keratinocytes stimulated with the pro-inflammatory cytokines IL-1β/TNFα. Activation of PBMC also leads to increased levels of both IL-1 ligands and their receptor, albeit to a lesser extent than observed in lesional psoriasis skin.

VIII. Biological Assays with IL-1δ or IL-1ε

Biological assays confirmed IFN-γ inducing activity by IL-1γ on T cells. IL-1γ stimulates production of IFN-γ by purified NK cells, and that induction is strongly synergized with IL-12 or IL-2. Similar biological activity should be exhibited by IL-1δ and/or IL-1ε or their antagonists.

The family of interleukins 1 contains molecules, each of which is an important mediator of inflammatory disease. For a comprehensive review, see Dinarello (1996) "Biologic basis for interleukin-1 in disease" *Blood* 87:2095–2147. There are indications that the various IL-1's play important roles in the initiation of disease, including the recently identified IGIF/IL-1γ (e.g., Rothe, et al. (1997) "Active stage of autoimmune diabetes is associated with the expression of a novel cytokine, IGIF, which is located near Idd2." *J. Clin. Invest.* 99:469–474. The finding of novel proteins related to the IL-1 family furthers the identification of molecules that provide the molecular basis for initiation of disease and allow for the development of therapeutic strategies of increased range and efficacy.

Similar biological assays as applied to other known members of the family should be performed with purified IL-1δ or IL-1ε.

IX. Preparation of Antibodies Specific for IL-1δ or IL-1ε

Inbred Balb/c mice are immunized intraperitoneally with recombinant forms of the protein, e.g., purified soluble IL-1δ-or IL-1ε-FLAG or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response.

Monoclonal antibodies may be made. For example, splenocytes are fused with an appropriate fusion partner and hybridomas are selected in growth medium by standard procedures. Hybridoma supernatants are screened for the presence of antibodies which bind to the desired IL-1γ, e.g., by ELISA or other assay. Antibodies which specifically recognize IL-1δ or IL-1ε may also be selected or prepared.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156–4160; Barry, et al. (1994) *BioTechniques* 16:616–619; and Xiang, et al. (1995) *Immunity* 2: 129–135.

X. Production of Fusion Proteins with IL-1δ or IL-1ε

Various fusion constructs are made with IL-1δ or IL-1ε. This portion of the gene is fused to an epitope tag, e.g., a FLAG tag, or to a two hybrid system construct. See, e.g., Fields and Song (1989) *Nature* 340:245–246.

The epitope tag may be used in an expression cloning procedure with detection with anti-FLAG antibodies to detect a binding partner, e.g., receptor for the respective IL-1. The two hybrid system may also be used to isolate proteins which specifically bind to IL-1δ or IL-1ε.

XI. Isolation of a Receptor for IL-1δ or IL-1ε

An IL-1δ can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods.

The binding composition is used to screen an expression library made from a cell line which expresses a binding partner, i.e., receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×105 cells per chamber in 1.5 ml of growth media. Incubate overnight at 37° C.

On day 1 for each sample, prepare 0.5 ml of a solution of 66 μg/ml DEAE-dextran, 66 μM chloroquine, and 4 μg DNA in serum free DME. For each set, a positive control is prepared, e.g., of IL-1γ-FLAG cDNA at 1 and ½00 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 μl/ml of 1 M NaN₃ for 20 min. Cells are then washed with HBSS/saponin 1×. Add appropriate IL-1δ or IL-1δ/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Evaluate positive staining of pools and progressively subclone to isolation of single genes responsible for the binding.

Alternatively, IL-1δ reagents are used to affinity purify or sort out cells expressing a receptor. See, e.g., Sambrook, et al., or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a IL-1δ fusion construct, or by use of antibodies raised against the first antibodies. Recursive cycles of selection and amplification lead to enrichment of appropriate clones and eventual isolation of receptor expressing clones.

Phage expression libraries can be screened by mammalian IL-1δ. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of inhibiting cutaneous inflammation comprising contacting a cell expressing IL-1R6 with an exogenous antagonist of mammalian IL-1ε (SEQ ID NO: 4 or 10) wherein the antagonist is:
   a) a antibody or antigen binding fragment thereof that specifically binds to IL-1ε or IL-1R6 (SEQ ID NO: 13 or 15); or
   b) IL-1δ (SEQ ID NO:2 or 11).

2. The method of claim 1, wherein the antibody or antigen binding fragment thereof neutralizes IL-1ε or IL-1R6.

3. The method of claim 1, wherein the cutaneous inflammation is psoriasis.

4. The method of claim 3, wherein the psoriasis is lesional psoriasis.

5. The method of claim 1, wherein the cell expressing IL-1R6 is selected from the group consisting of:
   a) a keratinocyte;
   b) a epithelial cell;
   c) a fibroblast cell; or
   d) a monocyte cell.

* * * * *

SEQUENCE LISTING

<160> NUMBER OF SEQ ID NOS: 15

<210> SEQ ID NO 1
<211> LENGTH: 1025
<212> TYPE: DNA
<213> ORGANISM: Homo sapiens
<220> FEATURE:
<221> NAME/KEY: CDS
<222> LOCATION: (58)..(522)
<223> OTHER INFORMATION:

<400> SEQUENCE: 1

```
gctcccgcca ggagaaagga acattctgag gggagtctac accctgtgga gctcaag          57 atg gtc ctg agt ggg gcg ctg tgc ttc cga atg aag gac tcg gca ttg      105
Met Val Leu Ser Gly Ala Leu Cys Phe Arg Met Lys Asp Ser Ala Leu
1               5                   10                  15 aag gtg ctt tat ctg cat aat aac cag ctt cta gct gga ggg ctg cat      153
Lys Val Leu Tyr Leu His Asn Asn Gln Leu Leu Ala Gly Gly Leu His
            20                  25                  30 gca ggg aag gtc att aaa ggt gaa gag atc agc gtg gtc ccc aat cgg      201
Ala Gly Lys Val Ile Lys Gly Glu Glu Ile Ser Val Val Pro Asn Arg
        35                  40                  45 tgg ctg gat gcc agc ctg tcc ccc gtc atc ctg ggt gtc cag ggt gga      249
Trp Leu Asp Ala Ser Leu Ser Pro Val Ile Leu Gly Val Gln Gly Gly
    50                  55                  60 agc cag tgc ctg tca tgt ggg gtg ggg cag gag ccg act cta aca cta      297
Ser Gln Cys Leu Ser Cys Gly Val Gly Gln Glu Pro Thr Leu Thr Leu
65                  70                  75                  80 gag cca gtg aac atc atg gag ctc tat ctt ggt gcc aag gaa tcc aag      345
Glu Pro Val Asn Ile Met Glu Leu Tyr Leu Gly Ala Lys Glu Ser Lys
                85                  90                  95
```

```
agc ttc acc ttc tac cgg cgg gac atg ggg ctc acc tcc agc ttc gag        393
Ser Phe Thr Phe Tyr Arg Arg Asp Met Gly Leu Thr Ser Ser Phe Glu
        100                 105                 110 tcg gct gcc tac ccg ggc tgg ttc ctg tgc acg gtg cct gaa gcc gat        441
Ser Ala Ala Tyr Pro Gly Trp Phe Leu Cys Thr Val Pro Glu Ala Asp
            115                 120                 125 cag cct gtc aga ctc acc cag ctt ccc gag aat ggt ggc tgg aat gcc        489
Gln Pro Val Arg Leu Thr Gln Leu Pro Glu Asn Gly Gly Trp Asn Ala
    130                 135                 140 ccc atc aca gac ttc tac ttc cag cag tgt gac tagggcaacg tgcccccag       542
Pro Ile Thr Asp Phe Tyr Phe Gln Gln Cys Asp
145                 150                 155 aactccctgg gcagagccag ctcgggtgag gggtgagtgg aggagaccca tggcggacaa      602
tcactctctc tgctctcagg accccacgt ctgacttagt gggcacctga ccactttgtc       662
ttctggttcc cagtttggat aaattctgag atttggagct cagtccacgg tcctccccca     722
ctggatggtg ctactgctgt ggaaccttgt aaaaaccatg tggggtaaac tgggaataac     782
atgaaaagat ttctgtgggg gtggggtggg gaagtggtgg ggaatcattc ctgcttaatg     842
gtaactgaca agtgttaccc tgagccccgc aggccaaccc atccccagtt gagccttata    902
gggtcagtag ctctccacat gaagtcctgt cactcaccac tgtgcaggaa gggaaggtgg    962
tcatagagta aggatctat ggcccttggc ccagccccac ccttcccctt taatcctgcc     1022
act                                                                    1025
```

<210> SEQ ID NO 2
<211> LENGTH: 155
<212> TYPE: PRT
<213> ORGANISM: Homo sapiens

<400> SEQUENCE: 2

```
Met Val Leu Ser Gly Ala Leu Cys Phe Arg Met Lys Asp Ser Ala Leu
1               5                   10                  15

Lys Val Leu Tyr Leu His Asn Asn Gln Leu Leu Ala Gly Gly Leu His
            20                  25                  30

Ala Gly Lys Val Ile Lys Gly Glu Glu Ile Ser Val Val Pro Asn Arg
        35                  40                  45

Trp Leu Asp Ala Ser Leu Ser Pro Val Ile Leu Gly Val Gln Gly Gly
    50                  55                  60

Ser Gln Cys Leu Ser Cys Gly Val Gly Gln Glu Pro Thr Leu Thr Leu
65                  70                  75                  80

Glu Pro Val Asn Ile Met Glu Leu Tyr Leu Gly Ala Lys Glu Ser Lys
                85                  90                  95

Ser Phe Thr Phe Tyr Arg Arg Asp Met Gly Leu Thr Ser Ser Phe Glu
            100                 105                 110

Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155
```

<210> SEQ ID NO 3
<211> LENGTH: 1073
<212> TYPE: DNA
<213> ORGANISM: Homo sapiens
<220> FEATURE:

<221> NAME/KEY: CDS
<222> LOCATION: (67)..(573)
<223> OTHER INFORMATION:

<400> SEQUENCE: 3

| | | |
|---|---|---:|
| ccacgattca gtccctgga ctgtagataa agacccttc ttgccaggtg ctgagacaac | | 60 |

| | | | | | | | | | | | | | | | |
|---|---|---|---|---|---|---|---|---|---|---|---|---|---|---|---:|
| cacact | atg | aga | ggc | act | cca | gga | gac | gct | gat | ggt | gga | gga | agg | gcc | 108 |
| | Met | Arg | Gly | Thr | Pro | Gly | Asp | Ala | Asp | Gly | Gly | Gly | Arg | Ala | |
| | 1 | | | 5 | | | | | 10 | | | | | | |

| | | | | | | | | | | | | | | |
|---|---|---|---|---|---|---|---|---|---|---|---|---|---|---|---:|
| gtc | tat | caa | tca | atg | tgt | aaa | cct | att | act | ggg | act | att | aat | gat ttg | 156 |
| Val | Tyr | Gln | Ser | Met | Cys | Lys | Pro | Ile | Thr | Gly | Thr | Ile | Asn | Asp Leu | |
| 15 | | | | 20 | | | | 25 | | | | | | 30 | |

| | | | | | | | | | | | | | | |
|---|---|---|---|---|---|---|---|---|---|---|---|---|---|---|---:|
| aat | cag | caa | gtg | tgg | acc | ctt | cag | ggt | cag | aac | ctt | gtg | gca | gtt cca | 204 |
| Asn | Gln | Gln | Val | Trp | Thr | Leu | Gln | Gly | Gln | Asn | Leu | Val | Ala | Val Pro | |
| | | | | 35 | | | | | 40 | | | | | 45 | |

| | | | | | | | | | | | | | | |
|---|---|---|---|---|---|---|---|---|---|---|---|---|---|---|---:|
| cga | agt | gac | agt | gtg | acc | cca | gtc | act | gtt | gct | gtt | atc | aca | tgc aag | 252 |
| Arg | Ser | Asp | Ser | Val | Thr | Pro | Val | Thr | Val | Ala | Val | Ile | Thr | Cys Lys | |
| | | | 50 | | | | | 55 | | | | | 60 | | |

| | | | | | | | | | | | | | | |
|---|---|---|---|---|---|---|---|---|---|---|---|---|---|---|---:|
| tat | cca | gag | gct | ctt | gag | caa | ggc | aga | ggg | gat | ccc | att | tat | ttg gga | 300 |
| Tyr | Pro | Glu | Ala | Leu | Glu | Gln | Gly | Arg | Gly | Asp | Pro | Ile | Tyr | Leu Gly | |
| | | 65 | | | | | 70 | | | | | 75 | | | |

| | | | | | | | | | | | | | | |
|---|---|---|---|---|---|---|---|---|---|---|---|---|---|---|---:|
| atc | cag | aat | cca | gaa | atg | tgt | ttg | tat | tgt | gag | aag | gtt | gga | gaa cag | 348 |
| Ile | Gln | Asn | Pro | Glu | Met | Cys | Leu | Tyr | Cys | Glu | Lys | Val | Gly | Glu Gln | |
| 80 | | | | | 85 | | | | | 90 | | | | | |

| | | | | | | | | | | | | | | |
|---|---|---|---|---|---|---|---|---|---|---|---|---|---|---|---:|
| ccc | aca | ttg | cag | cta | aaa | gag | cag | aag | atc | atg | gat | ctg | tat | ggc caa | 396 |
| Pro | Thr | Leu | Gln | Leu | Lys | Glu | Gln | Lys | Ile | Met | Asp | Leu | Tyr | Gly Gln | |
| 95 | | | | | 100 | | | | | 105 | | | | | 110 |

| | | | | | | | | | | | | | | |
|---|---|---|---|---|---|---|---|---|---|---|---|---|---|---|---:|
| ccc | gag | ccc | gtg | aaa | ccc | ttc | ctt | ttc | tac | cgt | gcc | aag | act | ggt agg | 444 |
| Pro | Glu | Pro | Val | Lys | Pro | Phe | Leu | Phe | Tyr | Arg | Ala | Lys | Thr | Gly Arg | |
| | | | 115 | | | | | 120 | | | | | 125 | | |

| | | | | | | | | | | | | | | |
|---|---|---|---|---|---|---|---|---|---|---|---|---|---|---|---:|
| acc | tcc | acc | ctt | gag | tct | gtg | gcc | ttc | ccg | gac | tgg | ttc | att | gcc tcc | 492 |
| Thr | Ser | Thr | Leu | Glu | Ser | Val | Ala | Phe | Pro | Asp | Trp | Phe | Ile | Ala Ser | |
| | | 130 | | | | | 135 | | | | | 140 | | | |

| | | | | | | | | | | | | | | |
|---|---|---|---|---|---|---|---|---|---|---|---|---|---|---|---:|
| tcc | aag | aga | gac | cag | ccc | atc | att | ctg | act | tca | gaa | ctt | ggg | aag tca | 540 |
| Ser | Lys | Arg | Asp | Gln | Pro | Ile | Ile | Leu | Thr | Ser | Glu | Leu | Gly | Lys Ser | |
| | 145 | | | | | 150 | | | | | 155 | | | | |

| | | | | | | | | | | |
|---|---|---|---|---|---|---|---|---|---|---|---:|
| tac | aac | act | gcc | ttt | gaa | tta | aat | ata | aat | gac tgaactcagc ctagaggtgg | 593 |
| Tyr | Asn | Thr | Ala | Phe | Glu | Leu | Asn | Ile | Asn | Asp | |
| 160 | | | | | 165 | | | | | | |

| | |
|---|---:|
| cagcttggtc tttgtcttaa agtttctggt tcccaatgtg ttttcgtcta cattttctta | 653 |
| gtgtcatttt cacgctggtg ctgagacagg ggcaaggctg ctgttatcat ctcattttat | 713 |
| aatgaagaag aagcaattac ttcatagcaa ctgaagaaca ggatgtggcc tcagaagcag | 773 |
| gagagctggg tggtataagg ctgtcctctc aagctggtgc tgtgtaggcc acaaggcatc | 833 |
| tgcatgagtg actttaagac tcaaagacca aacactgagc tttcttctag ggtgggtat | 893 |
| gaagatgctt cagagctcat gcgcgttacc cacgatggca tgactagcac agagctgatc | 953 |
| tctgtttctg ttttgcttta ttccctcttg ggatgatatc atccagtctt tatatgttgc | 1013 |
| caatatacct cattgtgtgt aatagaacct tcttagcatt aagaccttgt aaacaaaaat | 1073 |

<210> SEQ ID NO 4
<211> LENGTH: 169
<212> TYPE: PRT
<213> ORGANISM: Homo sapiens

<400> SEQUENCE: 4

Met Arg Gly Thr Pro Gly Asp Ala Asp Gly Gly Gly Arg Ala Val Tyr
1               5                   10                  15

```
Gln Ser Met Cys Lys Pro Ile Thr Gly Thr Ile Asn Asp Leu Asn Gln
             20                  25                  30

Gln Val Trp Thr Leu Gln Gly Gln Asn Leu Val Ala Val Pro Arg Ser
             35                  40                  45

Asp Ser Val Thr Pro Val Thr Val Ala Val Ile Thr Cys Lys Tyr Pro
50                       55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
             100                 105                 110

Pro Val Lys Pro Phe Leu Phe Tyr Arg Ala Lys Thr Gly Arg Thr Ser
             115                 120                 125

Thr Leu Glu Ser Val Ala Phe Pro Asp Trp Phe Ile Ala Ser Ser Lys
130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                 165
```

<210> SEQ ID NO 5
<211> LENGTH: 145
<212> TYPE: PRT
<213> ORGANISM: Homo sapiens

<400> SEQUENCE: 5

```
Met Arg Ile Ile Lys Tyr Glu Phe Ile Leu Asn Asp Ala Leu Asn Gln
1               5                   10                  15

Ser Ile Ile Arg Ala Asn Asp Gln Tyr Leu Thr Ala Ala Ala Leu His
             20                  25                  30

Asn Leu Asp Glu Ala Val Lys Phe Asp Met Gly Ala Tyr Lys Ser Ser
             35                  40                  45

Lys Asp Asp Ala Lys Ile Thr Val Ile Leu Arg Ile Ser Lys Thr Gln
50                       55                  60

Leu Tyr Val Thr Ala Gln Asp Glu Asp Gln Pro Val Leu Leu Lys Glu
65                  70                  75                  80

Met Pro Glu Ile Pro Lys Thr Ile Thr Gly Ser Glu Thr Asn Leu Leu
                 85                  90                  95

Phe Phe Trp Glu Thr His Gly Thr Lys Asn Tyr Phe Thr Ser Val Ala
             100                 105                 110

His Pro Asn Leu Phe Ile Ala Thr Lys Gln Asp Tyr Trp Val Cys Leu
             115                 120                 125

Ala Gly Gly Pro Pro Ser Ile Thr Asp Phe Gln Ile Leu Glu Asn Gln
130                 135                 140

Ala
145
```

<210> SEQ ID NO 6
<211> LENGTH: 153
<212> TYPE: PRT
<213> ORGANISM: Homo sapiens

<400> SEQUENCE: 6

```
Ala Pro Val Arg Ser Leu Asn Cys Thr Leu Arg Asp Ser Gln Gln Lys
1               5                   10                  15
```

-continued

Ser Leu Val Met Ser Gly Pro Tyr Glu Leu Lys Ala Leu His Leu Gln
          20              25              30

Gly Gln Asp Met Glu Gln Gln Val Val Phe Ser Met Ser Phe Val Gln
          35              40              45

Gly Glu Glu Ser Asn Asp Lys Ile Pro Val Ala Leu Gly Leu Lys Glu
50                  55                  60

Lys Asn Leu Tyr Leu Ser Cys Val Leu Lys Asp Asp Lys Pro Thr Leu
65              70                  75                  80

Gln Leu Glu Ser Val Asp Pro Lys Asn Tyr Pro Lys Lys Met Glu
              85                  90                  95

Lys Arg Phe Val Phe Asn Lys Ile Glu Ile Asn Asn Lys Leu Glu Phe
              100             105             110

Glu Ser Ala Gln Phe Pro Asn Trp Tyr Ile Ser Thr Ser Gln Ala Glu
          115             120             125

Asn Met Pro Val Phe Leu Gly Gly Thr Lys Gly Gln Asp Ile Thr
          130             135             140

Asp Phe Thr Met Gln Phe Val Ser Ser
145                 150

<210> SEQ ID NO 7
<211> LENGTH: 147
<212> TYPE: PRT
<213> ORGANISM: Homo sapiens

<400> SEQUENCE: 7

Lys Ser Ser Lys Met Gln Ala Phe Arg Ile Trp Asp Val Asn Gln Lys
1               5                   10                  15

Thr Phe Tyr Leu Arg Asn Asn Gln Leu Val Ala Gly Tyr Leu Gln Gly
              20                  25                  30

Pro Asn Val Asn Leu Glu Glu Lys Ile Asp Val Val Pro Ile Glu Pro
              35                  40                  45

His Ala Leu Phe Leu Gly Ile His Gly Gly Lys Met Cys Leu Ser Cys
          50                  55                  60

Val Lys Ser Gly Asp Glu Thr Arg Leu Gln Leu Glu Ala Val Asn Ile
65                  70                  75                  80

Thr Asp Leu Ser Glu Asn Arg Lys Gln Asp Lys Arg Phe Ala Phe Ile
              85                  90                  95

Arg Ser Asp Ser Gly Pro Thr Thr Ser Phe Glu Ser Ala Ala Cys Pro
              100                 105                 110

Gly Trp Phe Leu Cys Thr Ala Met Glu Ala Asp Gln Pro Val Ser Leu
          115                 120                 125

Thr Asn Met Pro Asp Glu Gly Val Met Val Thr Lys Phe Tyr Phe Gln
          130                 135                 140

Glu Asp Glu
145

<210> SEQ ID NO 8
<211> LENGTH: 157
<212> TYPE: PRT
<213> ORGANISM: Mus musculus

<400> SEQUENCE: 8

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
              20                  25                  30

-continued

```
Thr Asp Ile Asp Gln Ser Ala Ser Glu Pro Gln Thr Arg Leu Ile Ile
         35                  40                  45

Tyr Met Tyr Lys Asp Ser Glu Val Arg Gly Leu Ala Val Thr Leu Ser
 50                  55                  60

Val Lys Asp Ser Lys Met Ser Thr Leu Ser Cys Lys Asn Lys Ile Ile
 65                  70                  75                  80

Ser Phe Glu Glu Met Asp Pro Pro Glu Asn Ile Asp Asp Ile Gln Ser
                 85                  90                  95

Asp Leu Ile Phe Phe Gln Lys Arg Val Pro Gly His Asn Lys Met Glu
                100                 105                 110

Phe Glu Ser Ser Leu Tyr Glu Gly His Phe Leu Ala Cys Gln Lys Glu
                115                 120                 125

Asp Asp Ala Phe Lys Leu Ile Leu Lys Lys Asp Glu Asn Gly Asp
130                 135                 140

Lys Ser Val Met Phe Thr Leu Thr Asn Leu His Gln Ser
145                 150                 155

<210> SEQ ID NO 9
<211> LENGTH: 157
<212> TYPE: PRT
<213> ORGANISM: Homo sapiens

<400> SEQUENCE: 9

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
                 20                  25                  30

Met Thr Asp Ser Asp Cys Arg Asp Asn Ala Pro Arg Thr Ile Phe Ile
         35                  40                  45

Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp
145                 150                 155

<210> SEQ ID NO 10
<211> LENGTH: 157
<212> TYPE: PRT
<213> ORGANISM: Mus musculus

<400> SEQUENCE: 10

Glu Lys Glu Leu Arg Ala Ala Ser Pro Ser Leu Arg His Val Gln Asp
 1               5                  10                  15

Leu Ser Ser Arg Val Trp Ile Leu Gln Asn Asn Ile Leu Thr Ala Val
                 20                  25                  30

Pro Arg Lys Glu Gln Thr Val Pro Val Thr Ile Thr Leu Leu Pro Cys
         35                  40                  45
```

```
Gln Tyr Leu Asp Thr Leu Glu Thr Asn Arg Gly Asp Pro Thr Tyr Met
        50                  55                  60
Gly Val Gln Arg Pro Met Ser Cys Leu Phe Cys Thr Lys Asp Gly Glu
 65                  70                  75                  80
Gln Pro Val Leu Gln Leu Gly Glu Gly Asn Ile Met Glu Met Tyr Asn
                 85                  90                  95
Lys Lys Glu Pro Val Lys Ala Ser Leu Phe Tyr His Lys Lys Ser Gly
            100                 105                 110
Thr Thr Ser Thr Phe Glu Ser Ala Ala Phe Pro Gly Trp Phe Ile Ala
        115                 120                 125
Val Cys Ser Lys Gly Ser Cys Pro Leu Ile Leu Thr Gln Glu Leu Gly
    130                 135                 140
Glu Ile Phe Ile Thr Asp Phe Glu Met Ile Val Val His
145                 150                 155
```

```
<210> SEQ ID NO 11
<211> LENGTH: 154
<212> TYPE: PRT
<213> ORGANISM: Mus musculus

<400> SEQUENCE: 11
```

```
Val Leu Ser Gly Ala Leu Cys Phe Arg Met Lys Asp Ser Ala Leu Lys
 1               5                  10                  15
Val Leu Tyr Leu His Asn Asn Gln Leu Leu Ala Gly Gly Leu His Ala
            20                  25                  30
Glu Lys Val Ile Lys Gly Glu Glu Ile Ser Val Pro Asn Arg Ala
        35                  40                  45
Leu Asp Ala Ser Leu Ser Pro Val Ile Leu Gly Val Gln Gly Gly Ser
 50                  55                  60
Gln Cys Leu Ser Cys Gly Thr Glu Lys Gly Pro Ile Leu Lys Leu Glu
 65                  70                  75                  80
Pro Val Asn Ile Met Glu Leu Tyr Leu Gly Ala Lys Glu Ser Lys Ser
                 85                  90                  95
Phe Thr Pro Tyr Arg Arg Asp Met Gly Leu Thr Ser Ser Phe Glu Ser
            100                 105                 110
Ala Ala Tyr Pro Gly Trp Phe Leu Cys Thr Ser Pro Glu Ala Asp Gln
        115                 120                 125
Pro Val Arg Leu Thr Gln Ile Pro Glu Asp Pro Ala Trp Asp Ala Pro
    130                 135                 140
Ile Thr Asp Phe Tyr Phe Gln Gln Cys Asp
145                 150
```

```
<210> SEQ ID NO 12
<211> LENGTH: 1689
<212> TYPE: DNA
<213> ORGANISM: Homo sapiens
<220> FEATURE:
<221> NAME/KEY: CDS
<222> LOCATION: (1)..(1686)
<223> OTHER INFORMATION:

<400> SEQUENCE: 12
```

```
atg tgg tcc ttg ctg ctc tgc ggg ttg tcc atc gcc ctt cca ctg tct      48
Met Trp Ser Leu Leu Leu Cys Gly Leu Ser Ile Ala Leu Pro Leu Ser
 1               5                  10                  15 gtc aca gca gat gga tgc aag gac att ttt atg aaa aat gag ata ctt      96
Val Thr Ala Asp Gly Cys Lys Asp Ile Phe Met Lys Asn Glu Ile Leu
            20                  25                  30
```

| | | |
|---|---|---|
| tca gca agc cag cct ttt gct ttt aat tgt aca ttc cct ccc ata aca<br>Ser Ala Ser Gln Pro Phe Ala Phe Asn Cys Thr Phe Pro Pro Ile Thr<br>35          40              45 | 144 | |
| tct ggg gaa gtc agt gta aca tgg tat aaa aat tct agc aaa atc cca<br>Ser Gly Glu Val Ser Val Thr Trp Tyr Lys Asn Ser Ser Lys Ile Pro<br>50          55              60 | 192 | |
| gtg tcc aaa atc ata cag tct aga att cac cag gac gag act tgg att<br>Val Ser Lys Ile Ile Gln Ser Arg Ile His Gln Asp Glu Thr Trp Ile<br>65          70              75              80 | 240 | |
| ttg ttt ctc ccc atg gaa tgg ggg gac tca gga gtc tac caa tgt gtt<br>Leu Phe Leu Pro Met Glu Trp Gly Asp Ser Gly Val Tyr Gln Cys Val<br>           85              90              95 | 288 | |
| ata aag ggt aga gac agc tgt cat aga ata cat gta aac cta act gtt<br>Ile Lys Gly Arg Asp Ser Cys His Arg Ile His Val Asn Leu Thr Val<br>           100             105             110 | 336 | |
| ttt gaa aaa cat tgg tgt gac act tcc ata ggt ggt tta cca aat tta<br>Phe Glu Lys His Trp Cys Asp Thr Ser Ile Gly Gly Leu Pro Asn Leu<br>           115             120             125 | 384 | |
| tca gat gag tac aag caa ata tta cat ctt gga aaa gat gat agt ctc<br>Ser Asp Glu Tyr Lys Gln Ile Leu His Leu Gly Lys Asp Asp Ser Leu<br>130         135             140 | 432 | |
| aca tgt cat ctg cac ttc ccg aag agt tgt gtt ttg ggt cca ata aag<br>Thr Cys His Leu His Phe Pro Lys Ser Cys Val Leu Gly Pro Ile Lys<br>145         150             155             160 | 480 | |
| tgg tat aag gac tgt aac gag att aaa ggg gag cgg ttc act gtt ttg<br>Trp Tyr Lys Asp Cys Asn Glu Ile Lys Gly Glu Arg Phe Thr Val Leu<br>           165             170             175 | 528 | |
| gaa acc agg ctt ttg gtg agc aat gtc tcg gca gag gac aga ggg aac<br>Glu Thr Arg Leu Leu Val Ser Asn Val Ser Ala Glu Asp Arg Gly Asn<br>           180             185             190 | 576 | |
| tac gcg tgt caa gcc ata ctg aca cac tca ggg aag cag tac gag gtt<br>Tyr Ala Cys Gln Ala Ile Leu Thr His Ser Gly Lys Gln Tyr Glu Val<br>           195             200             205 | 624 | |
| tta aat ggc atc act gtg agc att aca gaa aga gct gga tat gga gga<br>Leu Asn Gly Ile Thr Val Ser Ile Thr Glu Arg Ala Gly Tyr Gly Gly<br>210         215             220 | 672 | |
| agt gtc cct aaa atc att tat cca aaa aat cat tca att gaa gta cag<br>Ser Val Pro Lys Ile Ile Tyr Pro Lys Asn His Ser Ile Glu Val Gln<br>225         230             235             240 | 720 | |
| ctt ggt acc act ctg att gtg gac tgc aat gta aca gac acc aag gat<br>Leu Gly Thr Thr Leu Ile Val Asp Cys Asn Val Thr Asp Thr Lys Asp<br>           245             250             255 | 768 | |
| aat aca aat cta cga tgc tgg aga gtc aat aac act ttg gtg gat gat<br>Asn Thr Asn Leu Arg Cys Trp Arg Val Asn Asn Thr Leu Val Asp Asp<br>           260             265             270 | 816 | |
| tac tat gat gaa tcc aaa cga atc aga gaa ggg gtg gaa acc cat gtc<br>Tyr Tyr Asp Glu Ser Lys Arg Ile Arg Glu Gly Val Glu Thr His Val<br>           275             280             285 | 864 | |
| tct ttt cgg gaa cat aat ttg tac aca gta aac atc acc ttc ttg gaa<br>Ser Phe Arg Glu His Asn Leu Tyr Thr Val Asn Ile Thr Phe Leu Glu<br>290         295             300 | 912 | |
| gtg aaa atg gaa gat tat ggc ctt cct ttc atg tgc cac gct gga gtg<br>Val Lys Met Glu Asp Tyr Gly Leu Pro Phe Met Cys His Ala Gly Val<br>305         310             315             320 | 960 | |
| tcc aca gca tac att ata tta cag ctc cca gct ccg gat ttt cga gct<br>Ser Thr Ala Tyr Ile Ile Leu Gln Leu Pro Ala Pro Asp Phe Arg Ala<br>           325             330             335 | 1008 | |
| tac ttg ata gga ggg ctt atc gcc ttg gtg gct gtg gct gtg tct gtt<br>Tyr Leu Ile Gly Gly Leu Ile Ala Leu Val Ala Val Ala Val Ser Val<br>           340             345             350 | 1056 | |

```
gtg tac ata tac aac att ttt aag atc gac att gtt ctt tgg tat cga      1104
Val Tyr Ile Tyr Asn Ile Phe Lys Ile Asp Ile Val Leu Trp Tyr Arg
            355                 360                 365 agt gcc ttc cat tct aca gag acc ata gta gat ggg aag ctg tat gac      1152
Ser Ala Phe His Ser Thr Glu Thr Ile Val Asp Gly Lys Leu Tyr Asp
370                 375                 380 gcc tat gtc tta tac ccc aag ccc cac aag gaa agc cag agg cat gcc      1200
Ala Tyr Val Leu Tyr Pro Lys Pro His Lys Glu Ser Gln Arg His Ala
385                 390                 395                 400 gtg gat gcc ctg gtg ttg aat atc ctg ccc gag gtg ttg gag aga caa      1248
Val Asp Ala Leu Val Leu Asn Ile Leu Pro Glu Val Leu Glu Arg Gln
            405                 410                 415 tgt gga tat aag ttg ttt ata ttc ggc aga gat gaa ttc cct gga caa      1296
Cys Gly Tyr Lys Leu Phe Ile Phe Gly Arg Asp Glu Phe Pro Gly Gln
        420                 425                 430 gcc gtg gcc aat gtc atc gat gaa aac gtt aag ctg tgc agg agg ctg      1344
Ala Val Ala Asn Val Ile Asp Glu Asn Val Lys Leu Cys Arg Arg Leu
    435                 440                 445 att gtc att gtg gtc ccc gaa tcg ctg ggc ttt ggc ctg ttg aag aac      1392
Ile Val Ile Val Val Pro Glu Ser Leu Gly Phe Gly Leu Leu Lys Asn
450                 455                 460 ctg tca gaa gaa caa atc gcg gtc tac agt gcc ctg atc cag gac ggg      1440
Leu Ser Glu Glu Gln Ile Ala Val Tyr Ser Ala Leu Ile Gln Asp Gly
465                 470                 475                 480 atg aag gtt att ctc att gag ctg gag aaa atc gag gac tac aca gtc      1488
Met Lys Val Ile Leu Ile Glu Leu Glu Lys Ile Glu Asp Tyr Thr Val
            485                 490                 495 atg cca gag tca att cag tac atc aaa cag aag cat ggt gcc atc cgg      1536
Met Pro Glu Ser Ile Gln Tyr Ile Lys Gln Lys His Gly Ala Ile Arg
        500                 505                 510 tgg cat ggg gac ttc acg gag cag tca cag tgt atg aag acc aag ttt      1584
Trp His Gly Asp Phe Thr Glu Gln Ser Gln Cys Met Lys Thr Lys Phe
    515                 520                 525 tgg aag aca gtg aga tac cac atg ccg ccc aga agg tgt cgg ccg ttt      1632
Trp Lys Thr Val Arg Tyr His Met Pro Pro Arg Arg Cys Arg Pro Phe
530                 535                 540 ctc cgg tcc acg tgc cgc agc aca cac ctc tgt acc gca ccg cag gcc      1680
Leu Arg Ser Thr Cys Arg Ser Thr His Leu Cys Thr Ala Pro Gln Ala
545                 550                 555                 560 cag aac tag                                                          1689
Gln Asn

SEQ ID NO 13
LENGTH: 562

<212> TYPE: PRT
<213> ORGANISM: Homo sapiens

<400> SEQUENCE: 13

Met Trp Ser Leu Leu Leu Cys Gly Leu Ser Ile Ala Leu Pro Leu Ser
1               5                   10                  15

Val Thr Ala Asp Gly Cys Lys Asp Ile Phe Met Lys Asn Glu Ile Leu
            20                  25                  30

Ser Ala Ser Gln Pro Phe Ala Phe Asn Cys Thr Phe Pro Pro Ile Thr
        35                  40                  45

Ser Gly Glu Val Ser Val Thr Trp Tyr Lys Asn Ser Ser Lys Ile Pro
    50                  55                  60

Val Ser Lys Ile Ile Gln Ser Arg Ile His Gln Asp Glu Thr Trp Ile
65                  70                  75                  80
```

```
Leu Phe Leu Pro Met Glu Trp Gly Asp Ser Gly Val Tyr Gln Cys Val
                85                  90                  95

Ile Lys Gly Arg Asp Ser Cys His Arg Ile His Val Asn Leu Thr Val
            100                 105                 110

Phe Glu Lys His Trp Cys Asp Thr Ser Ile Gly Gly Leu Pro Asn Leu
        115                 120                 125

Ser Asp Glu Tyr Lys Gln Ile Leu His Leu Gly Lys Asp Asp Ser Leu
    130                 135                 140

Thr Cys His Leu His Phe Pro Lys Ser Cys Val Leu Gly Pro Ile Lys
145                 150                 155                 160

Trp Tyr Lys Asp Cys Asn Glu Ile Lys Gly Glu Arg Phe Thr Val Leu
                165                 170                 175

Glu Thr Arg Leu Leu Val Ser Asn Val Ser Ala Glu Asp Arg Gly Asn
            180                 185                 190

Tyr Ala Cys Gln Ala Ile Leu Thr His Ser Gly Lys Gln Tyr Glu Val
        195                 200                 205

Leu Asn Gly Ile Thr Val Ser Ile Thr Glu Arg Ala Gly Tyr Gly Gly
    210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270

Tyr Tyr Asp Glu Ser Lys Arg Ile Arg Glu Gly Val Glu Thr His Val
        275                 280                 285

Ser Phe Arg Glu His Asn Leu Tyr Thr Val Asn Ile Thr Phe Leu Glu
    290                 295                 300

Val Lys Met Glu Asp Tyr Gly Leu Pro Phe Met Cys His Ala Gly Val
305                 310                 315                 320

Ser Thr Ala Tyr Ile Ile Leu Gln Leu Pro Ala Pro Asp Phe Arg Ala
                325                 330                 335

Tyr Leu Ile Gly Gly Leu Ile Ala Leu Val Ala Val Ala Val Ser Val
            340                 345                 350

Val Tyr Ile Tyr Asn Ile Phe Lys Ile Asp Ile Val Leu Trp Tyr Arg
        355                 360                 365

Ser Ala Phe His Ser Thr Glu Thr Ile Val Asp Gly Lys Leu Tyr Asp
    370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
            420                 425                 430

Ala Val Ala Asn Val Ile Asp Glu Asn Val Lys Leu Cys Arg Arg Leu
        435                 440                 445

Ile Val Ile Val Val Pro Glu Ser Leu Gly Phe Gly Leu Leu Lys Asn
    450                 455                 460

Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495
```

```
Met Pro Glu Ser Ile Gln Tyr Ile Lys Gln Lys His Gly Ala Ile Arg
                500                 505                 510

Trp His Gly Asp Phe Thr Glu Gln Ser Gln Cys Met Lys Thr Lys Phe
            515                 520                 525

Trp Lys Thr Val Arg Tyr His Met Pro Pro Arg Arg Cys Arg Pro Phe
        530                 535                 540

Leu Arg Ser Thr Cys Arg Ser Thr His Leu Cys Thr Ala Pro Gln Ala
545                 550                 555                 560

Gln Asn

<210> SEQ ID NO 14
<211> LENGTH: 1686
<212> TYPE: DNA
<213> ORGANISM: Rattus sp.
<220> FEATURE:
<221> NAME/KEY: CDS
<222> LOCATION: (1)..(1683)
<223> OTHER INFORMATION:

<400> SEQUENCE: 14 atg ggg atg cca ccc ttg ctc ttc tgt tgg gtg tct ttc gtg ctt cca      48
Met Gly Met Pro Pro Leu Leu Phe Cys Trp Val Ser Phe Val Leu Pro
1               5                   10                  15 ctt ttt gtg gca gca ggt aac tgt act gat gtc tat atg cac cat gag     96
Leu Phe Val Ala Ala Gly Asn Cys Thr Asp Val Tyr Met His His Glu
            20                  25                  30 atg att tca gag ggc cag cct ttc ccc ttc aac tgc aca tac cct cca    144
Met Ile Ser Glu Gly Gln Pro Phe Pro Phe Asn Cys Thr Tyr Pro Pro
        35                  40                  45 gta aca aac ggg gca gtg aat ctg aca tgg cat aga aca ccc agt aag    192
Val Thr Asn Gly Ala Val Asn Leu Thr Trp His Arg Thr Pro Ser Lys
    50                  55                  60 agc cca atc tcc atc aac aga cac gtt aga att cac cag gac cag tcc    240
Ser Pro Ile Ser Ile Asn Arg His Val Arg Ile His Gln Asp Gln Ser
65                  70                  75                  80 tgg att ttg ttt ctt ccg ttg gca ttg gag gac tca ggc atc tat caa    288
Trp Ile Leu Phe Leu Pro Leu Ala Leu Glu Asp Ser Gly Ile Tyr Gln
                85                  90                  95 tgt gtt ata aag gat gcc cac agc tgt tac cga ata gct ata aac cta    336
Cys Val Ile Lys Asp Ala His Ser Cys Tyr Arg Ile Ala Ile Asn Leu
            100                 105                 110 acc gtt ttt aga aaa cac tgg tgc gac tct tcc aac gaa gag agt tcc    384
Thr Val Phe Arg Lys His Trp Cys Asp Ser Ser Asn Glu Glu Ser Ser
        115                 120                 125 ata aat tcc tca gat gag tac cag caa tgg tta ccc ata gga aaa tcg    432
Ile Asn Ser Ser Asp Glu Tyr Gln Gln Trp Leu Pro Ile Gly Lys Ser
    130                 135                 140 ggc agt ctg acg tgc cat ctc tac ttc cca gag agc tgt gtt ttg gat    480
Gly Ser Leu Thr Cys His Leu Tyr Phe Pro Glu Ser Cys Val Leu Asp
145                 150                 155                 160 tca ata aag tgg tat aag ggt tgt gaa gag att aaa gtg agc aag aag    528
Ser Ile Lys Trp Tyr Lys Gly Cys Glu Glu Ile Lys Val Ser Lys Lys
                165                 170                 175 ttt tgc cct aca gga aca aag ctt ctt gtt aac aac atc gac gtg gag    576
Phe Cys Pro Thr Gly Thr Lys Leu Leu Val Asn Asn Ile Asp Val Glu
            180                 185                 190 gat agt ggg agc tat gca tgc tca gcc aga ctg aca cac ttg ggg aga    624
Asp Ser Gly Ser Tyr Ala Cys Ser Ala Arg Leu Thr His Leu Gly Arg
        195                 200                 205 atc ttc acg gtt aga aac tac att gct gtg aat acc aag gaa gtt ggg    672
```

-continued

| | | |
|---|---|---|
| Ile Phe Thr Val Arg Asn Tyr Ile Ala Val Asn Thr Lys Glu Val Gly<br>210 215 220 | | |
| tct gga gga agg atc cct aac atc acg tat cca aaa aac aac tcc att<br>Ser Gly Gly Arg Ile Pro Asn Ile Thr Tyr Pro Lys Asn Asn Ser Ile<br>225 230 235 240 | 720 | |
| gaa gtt caa ctt ggc tcc acc ctc att gtg gac tgc aat ata aca gac<br>Glu Val Gln Leu Gly Ser Thr Leu Ile Val Asp Cys Asn Ile Thr Asp<br>245 250 255 | 768 | |
| acg aag gag aat acg aac ctc aga tgc tgg cga gtt aac aac acc ctg<br>Thr Lys Glu Asn Thr Asn Leu Arg Cys Trp Arg Val Asn Asn Thr Leu<br>260 265 270 | 816 | |
| gtg gac gat tac tac aac gac ttc aaa cgc atc cag gaa gga atc gaa<br>Val Asp Asp Tyr Tyr Asn Asp Phe Lys Arg Ile Gln Glu Gly Ile Glu<br>275 280 285 | 864 | |
| acc aat ctg tct ctg agg aat cac att ctg tac aca gtg aac ata aca<br>Thr Asn Leu Ser Leu Arg Asn His Ile Leu Tyr Thr Val Asn Ile Thr<br>290 295 300 | 912 | |
| ttc tta gaa gtg aaa atg gag gac tac ggc cat cct ttc aca tgc cac<br>Phe Leu Glu Val Lys Met Glu Asp Tyr Gly His Pro Phe Thr Cys His<br>305 310 315 320 | 960 | |
| gct gcg gtg tcc gca gcc tac atc att ctg aaa cgc cca gct cca gac<br>Ala Ala Val Ser Ala Ala Tyr Ile Ile Leu Lys Arg Pro Ala Pro Asp<br>325 330 335 | 1008 | |
| ttc cgg gct tac ctc ata gga ggt ctc atg gct ttc cta ctt ctg gcc<br>Phe Arg Ala Tyr Leu Ile Gly Gly Leu Met Ala Phe Leu Leu Leu Ala<br>340 345 350 | 1056 | |
| gtg tcc att ctg tac atc tac aac acc ttt aag gtc gac atc gtg ctt<br>Val Ser Ile Leu Tyr Ile Tyr Asn Thr Phe Lys Val Asp Ile Val Leu<br>355 360 365 | 1104 | |
| tgg tat agg agt acc ttc cac act gcc cag gct cca gat gac gag aag<br>Trp Tyr Arg Ser Thr Phe His Thr Ala Gln Ala Pro Asp Asp Glu Lys<br>370 375 380 | 1152 | |
| ctg tat gat gcc tat gtc tta tac ccc aag tac cca aga gaa agc cag<br>Leu Tyr Asp Ala Tyr Val Leu Tyr Pro Lys Tyr Pro Arg Glu Ser Gln<br>385 390 395 400 | 1200 | |
| ggc cat gat gtg gac aca ctg gtg ttg aag atc ttg ccc gag gtg ctg<br>Gly His Asp Val Asp Thr Leu Val Leu Lys Ile Leu Pro Glu Val Leu<br>405 410 415 | 1248 | |
| gag aaa cag tgt gga tat aag tta ttc ata ttt ggc agg gat gaa ttc<br>Glu Lys Gln Cys Gly Tyr Lys Leu Phe Ile Phe Gly Arg Asp Glu Phe<br>420 425 430 | 1296 | |
| cct gga caa gct gtg gcc agc gtc att gat gaa aac att aag ctg tgt<br>Pro Gly Gln Ala Val Ala Ser Val Ile Asp Glu Asn Ile Lys Leu Cys<br>435 440 445 | 1344 | |
| agg agg ctg atg gtc ctc gtg gca cca gag aca tcc agc ttc agc ttt<br>Arg Arg Leu Met Val Leu Val Ala Pro Glu Thr Ser Ser Phe Ser Phe<br>450 455 460 | 1392 | |
| ctg aag aac ttg act gaa gaa caa atc gct gtc tac aat gcc ctc gtc<br>Leu Lys Asn Leu Thr Glu Glu Gln Ile Ala Val Tyr Asn Ala Leu Val<br>465 470 475 480 | 1440 | |
| cag gac ggc atg aag gtc att ctg att gaa ctg gag aga gtc aag gac<br>Gln Asp Gly Met Lys Val Ile Leu Ile Glu Leu Glu Arg Val Lys Asp<br>485 490 495 | 1488 | |
| tac agc acc atg ccc gag tcc att cag tac atc cga cag aag cac ggg<br>Tyr Ser Thr Met Pro Glu Ser Ile Gln Tyr Ile Arg Gln Lys His Gly<br>500 505 510 | 1536 | |
| gcc atc cag tgg gat ggg gac ttc aca gag cag gca cag tgc gcc aag<br>Ala Ile Gln Trp Asp Gly Asp Phe Thr Glu Gln Ala Gln Cys Ala Lys<br>515 520 525 | 1584 | |

```
acg aaa ttc tgg aag aaa gtg aga tat cat atg cca ccc agg agg tac    1632
Thr Lys Phe Trp Lys Lys Val Arg Tyr His Met Pro Pro Arg Arg Tyr
530                 535                 540 ccg gca tct ccc ccc gtc cag ctg cta gga cac aca ccc cgc ata cca    1680
Pro Ala Ser Pro Pro Val Gln Leu Leu Gly His Thr Pro Arg Ile Pro
545                 550                 555                 560 ggc tag                                                             1686
Gly

<210> SEQ ID NO 15
<211> LENGTH: 561
<212> TYPE: PRT
<213> ORGANISM: Rattus sp.

<400> SEQUENCE: 15

Met Gly Met Pro Pro Leu Leu Phe Cys Trp Val Ser Phe Val Leu Pro
1               5                   10                  15

Leu Phe Val Ala Ala Gly Asn Cys Thr Asp Val Tyr Met His His Glu
            20                  25                  30

Met Ile Ser Glu Gly Gln Pro Phe Pro Phe Asn Cys Thr Tyr Pro Pro
        35                  40                  45

Val Thr Asn Gly Ala Val Asn Leu Thr Trp His Arg Thr Pro Ser Lys
    50                  55                  60

Ser Pro Ile Ser Ile Asn Arg His Val Arg Ile His Gln Asp Gln Ser
65                  70                  75                  80

Trp Ile Leu Phe Leu Pro Leu Ala Leu Glu Asp Ser Gly Ile Tyr Gln
                85                  90                  95

Cys Val Ile Lys Asp Ala His Ser Cys Tyr Arg Ile Ala Ile Asn Leu
            100                 105                 110

Thr Val Phe Arg Lys His Trp Cys Asp Ser Ser Asn Glu Ser Ser
        115                 120                 125

Ile Asn Ser Ser Asp Glu Tyr Gln Gln Trp Leu Pro Ile Gly Lys Ser
    130                 135                 140

Gly Ser Leu Thr Cys His Leu Tyr Phe Pro Glu Ser Cys Val Leu Asp
145                 150                 155                 160

Ser Ile Lys Trp Tyr Lys Gly Cys Glu Glu Ile Lys Val Ser Lys Lys
                165                 170                 175

Phe Cys Pro Thr Gly Thr Lys Leu Leu Val Asn Asn Ile Asp Val Glu
            180                 185                 190

Asp Ser Gly Ser Tyr Ala Cys Ser Ala Arg Leu Thr His Leu Gly Arg
        195                 200                 205

Ile Phe Thr Val Arg Asn Tyr Ile Ala Val Asn Thr Lys Glu Val Gly
    210                 215                 220

Ser Gly Gly Arg Ile Pro Asn Ile Thr Tyr Pro Lys Asn Asn Ser Ile
225                 230                 235                 240

Glu Val Gln Leu Gly Ser Thr Leu Ile Val Asp Cys Asn Ile Thr Asp
                245                 250                 255

Thr Lys Glu Asn Thr Asn Leu Arg Cys Trp Arg Val Asn Asn Thr Leu
            260                 265                 270

Val Asp Asp Tyr Tyr Asn Asp Phe Lys Arg Ile Gln Glu Gly Ile Glu
        275                 280                 285

Thr Asn Leu Ser Leu Arg Asn His Ile Leu Tyr Thr Val Asn Ile Thr
    290                 295                 300

Phe Leu Glu Val Lys Met Glu Asp Tyr Gly His Pro Phe Thr Cys His
305                 310                 315                 320
```

-continued

```
Ala Ala Val Ser Ala Ala Tyr Ile Ile Leu Lys Arg Pro Ala Pro Asp
            325                 330                 335

Phe Arg Ala Tyr Leu Ile Gly Gly Leu Met Ala Phe Leu Leu Leu Ala
            340                 345                 350

Val Ser Ile Leu Tyr Ile Tyr Asn Thr Phe Lys Val Asp Ile Val Leu
            355                 360                 365

Trp Tyr Arg Ser Thr Phe His Thr Ala Gln Ala Pro Asp Asp Glu Lys
    370                 375                 380

Leu Tyr Asp Ala Tyr Val Leu Tyr Pro Lys Tyr Pro Arg Glu Ser Gln
385                 390                 395                 400

Gly His Asp Val Asp Thr Leu Val Leu Lys Ile Leu Pro Glu Val Leu
                405                 410                 415

Glu Lys Gln Cys Gly Tyr Lys Leu Phe Ile Phe Gly Arg Asp Glu Phe
                420                 425                 430

Pro Gly Gln Ala Val Ala Ser Val Ile Asp Glu Asn Ile Lys Leu Cys
            435                 440                 445

Arg Arg Leu Met Val Leu Val Ala Pro Glu Thr Ser Ser Phe Ser Phe
    450                 455                 460

Leu Lys Asn Leu Thr Glu Glu Gln Ile Ala Val Tyr Asn Ala Leu Val
465                 470                 475                 480

Gln Asp Gly Met Lys Val Ile Leu Ile Glu Leu Glu Arg Val Lys Asp
                485                 490                 495

Tyr Ser Thr Met Pro Glu Ser Ile Gln Tyr Ile Arg Gln Lys His Gly
            500                 505                 510

Ala Ile Gln Trp Asp Gly Asp Phe Thr Glu Gln Ala Gln Cys Ala Lys
            515                 520                 525

Thr Lys Phe Trp Lys Lys Val Arg Tyr His Met Pro Pro Arg Arg Tyr
    530                 535                 540

Pro Ala Ser Pro Pro Val Gln Leu Leu Gly His Thr Pro Arg Ile Pro
545                 550                 555                 560

Gly
```